(12) United States Patent
McCabe et al.

(10) Patent No.: US 10,716,628 B2
(45) Date of Patent: Jul. 21, 2020

(54) SYSTEMS, METHODS AND DEVICES FOR CALCULATING HIP CENTER OF ROTATION, ADJUSTING PARAMETERS OF JOINT REPLACEMENT FOR PELVIC TILT AND CALCULATING LEG LENGTH AND OFFSET

(71) Applicant: INTELLIJOINT SURGICAL INC., Waterloo (CA)

(72) Inventors: Samantha McCabe, Kitchener (CA); Kirsten Galea, Fergus (CA); Kevin Morency, Guelph (CA); Andre Novomir Hladio, Ottawa (CA); Richard Tyler Fanson, Kitchener (CA)

(73) Assignee: INTELLIJOINT SURGICAL INC., Kitchener (CA)

(*) Notice: Subject to any disclaimer, the term of this patent is extended or adjusted under 35 U.S.C. 154(b) by 937 days.

(21) Appl. No.: 15/337,409

(22) Filed: Oct. 28, 2016

(65) Prior Publication Data
US 2017/0119475 A1    May 4, 2017

Related U.S. Application Data

(60) Provisional application No. 62/248,079, filed on Oct. 29, 2015.

(51) Int. Cl.
*A61B 34/20* (2016.01)
*A61F 2/34* (2006.01)
(Continued)

(52) U.S. Cl.
CPC .............. *A61B 34/20* (2016.02); *A61B 5/066* (2013.01); *A61B 5/4571* (2013.01); *A61F 2/34* (2013.01); *A61F 2/4609* (2013.01); *A61F 2/4657* (2013.01); *A61B 5/1071* (2013.01); *A61B 2034/2048* (2016.02); *A61B 2034/2055* (2016.02); *A61B 2034/2065* (2016.02); *A61B 2034/2072* (2016.02); *A61B 2034/254* (2016.02); *A61B 2090/373* (2016.02);
(Continued)

(58) Field of Classification Search
CPC .... A61B 2034/2048; A61B 2034/2055; A61B 2034/2065; A61B 2034/2072; A61B 2034/254; A61B 2090/373; A61B 2505/05; A61B 34/20; A61B 5/066; A61B 5/1071; A61B 5/4571; A61F 2002/4658; A61F 2002/4668; A61F 2/34; A61F 2/4609; A61F 2/4657
See application file for complete search history.

(56) References Cited

U.S. PATENT DOCUMENTS

2008/0214960 A1* 9/2008 Hodgson ............. A61B 17/175
                                                      600/587
2015/0038832 A1* 2/2015 Bettenga ............. A61B 5/6878
                                                      600/424

* cited by examiner

*Primary Examiner* — Michael T Rozanski

(57) ABSTRACT

Systems and methods are described herein to calculate implant orientation measurements of an acetabular cup implant in hip replacement surgery, such surgery performed with minimally invasive incisions. Surgeons may obtain real-time updated implant orientation measurements that compensate for pelvic tilt of a patient, such tilt measured pre-operatively. Implant orientation measurements may be measured from the patient's anterior pelvic plane, supine coronal plane, standing coronal plane or any other reference plane that the surgeon may find useful. Also disclosed are systems, methods and devices to measure hip center of rotation and provide leg length and offset measurements in hip replacement surgery.

21 Claims, 27 Drawing Sheets

(51) Int. Cl.
*A61F 2/46* (2006.01)
*A61B 5/026* (2006.01)
*A61B 5/06* (2006.01)
*A61B 5/00* (2006.01)
A61B 90/00 (2016.01)
A61B 34/00 (2016.01)
A61B 5/107 (2006.01)

(52) U.S. Cl.
CPC ... *A61B 2505/05* (2013.01); *A61F 2002/4658* (2013.01); *A61F 2002/4668* (2013.01)

SYSTEMS, METHODS AND DEVICES FOR CALCULATING HIP CENTER OF ROTATION, ADJUSTING PARAMETERS OF JOINT REPLACEMENT FOR PELVIC TILT AND CALCULATING LEG LENGTH AND OFFSET

CROSS-REFERENCE TO RELATED APPLICATIONS

This application claims the benefit of U.S. provisional application No. 62/248,079 titled "Systems, methods and devices for calculating hip center of rotation and adjusting for pelvic tilt" and filed on Oct. 29, 2015, the entire contents of which are incorporated herein by reference.

FIELD

The present application generally relates to Total Hip Arthroplasty (THA) with a minimally invasive surgical approach. Systems, methods and devices are described herein to calculate parameters such as hip center of rotation, leg length and offset and implant orientation measurements of a prosthetic implant with respect to an anatomy of a patient.

BACKGROUND

During THA, ensuring proper alignment of an acetabular component or implant with respect to a pelvis of a patient is important. The acetabular cup implant has to be properly positioned, preferably with respect to predefined and generally accepted anatomical reference planes of the pelvis such as the anterior pelvic plane (APP). The acetabular implant and the femoral implant form the artificial hip joint. Alignment of these prosthetic components has typically been performed relying solely on a surgeon's judgment of their spatial location. Studies have shown that failure to properly align the acetabular components or implant with the pelvis may lead to premature wear, propensity to dislocate and patient discomfort. Intra-operative surgical navigation systems and methods can assist surgeons in providing guidance in the placement of the prosthesis in the body of the patient to improve clinical outcomes.

These intra-operative surgical navigation systems and methods may identify anatomical planes by localizing a patient's bony landmarks to assist in the 3D spatial localization of prosthetic components. Depending on the surgical approach taken, different challenges of spatial localization arise as the availability of bony landmarks differs with the approach.

Surgical navigations systems and various embodiments are described in U.S. patent publication No. 20120157887 entitled "Method and system for aligning a prosthesis during surgery" and U.S. patent publication No. 20160249987 entitled "Systems, methods and devices for anatomical registration and surgical localization", the entire contents of which are incorporated herein by reference.

BRIEF SUMMARY

There is disclosed an electronic guidance system to provide intra-operative anatomic measurements to guide placement of an implant with respect to an anatomy of a patient. The system comprises an optical sensor to generate and communicate image data of respective targets attached to a probe tool and a surgical tool to track the probe tool and the surgical tool during an implant placement procedure and an intra-operative computing unit communicatively coupled to the optical sensor. The computing unit is configured to register a first reference plane for the anatomy of the patient in a defined coordinate system using the respective image data from the probe tool, where the probe tool points to at least three reference locations on the anatomy to define the first reference plane, receive optionally an inputted tilt angle of the anatomy of the patient relative to a second plane within the defined coordinate system. If the inputted tilt angle is received, the computing unit is configured to generate a second reference plane for the anatomy of the patient using the inputted tilt angle and the first reference plane and determine implant orientation measurements using the respective image data from the surgical tool as it is tracked during the implant placement procedure while referencing the implant orientation measurements relative to the second reference plane. The computing unit then displays, in a graphical user interface, the implant orientation measurements relative to the second reference plane. The electronic guidance system is further configured to determine implant orientation measurements using the respective image data from the surgical tool as it is tracked, referencing the implant orientation measurements to the reference plane for the anatomy of the patient without using the inputted tilt angle; and display in a graphical user interface the implant orientation measurements relative to the first reference plane.

The electronic guidance system may further comprise an inclination sensor to generate and communicate inclination measurements to track the anatomy of the patient during the implant placement procedure where changes in inclination of the inclination sensor correspond to changes in inclination of the anatomy of the patient and the computing unit is further configured to register a positional plane for the anatomy of the patient in the defined coordinate system using the inclination measurements, equating the positional plane to a horizontal plane within the defined coordinate system. The intra-operative computing unit is further configured to calculate and display a tilt angle of the anatomy of the patient relative to the horizontal plane using the first reference plane and the positional plane. The second plane is a standing coronal plane. The anatomy of the patient is a pelvis. Where the anatomy is a pelvis, the inputted tilt angle is a pelvic tilt determined from a pre-operative medical image of the pelvis. The first reference plane is the anterior pelvic plane determined when the patient is in a supine position. The intra-operative computing unit is further configured to provide a graphical user interface to receive and display the inputted tilt angle. The intra-operative computing unit is further configured to receive the inputted tilt angle from an image analyzer communicatively connected to the intra-operative computing unit.

There is disclosed herein an electronic guidance system to provide intra-operative anatomic measurements to guide placement of an implant with respect to an anatomy of a patient, the electronic guidance system comprising an optical sensor to generate and communicate image data of respective targets attached to a probe tool and a surgical tool to track the probe tool and the surgical tool during an implant placement procedure; an inclination sensor to generate and communicate inclination measurements where changes in inclination of the sensor correspond to changes in inclination of the anatomy of the patient to track anatomy of the patient during the implant placement procedure; and an intra-operative computing unit communicatively coupled to the optical sensor and the inclination sensor, the intra-operative computing unit configured to register a positional plane for the anatomy of the patient in a defined coordinate system using the inclination measurements, equating the positional plane to a horizontal plane within the defined coordinate system; receive optionally an inputted tilt angle of the anatomy of the patient relative to a second plane within the defined coordinate system. If the inputted tilt angle is received, the computing unit is configured to generate a second reference plane for the anatomy of the patient using the inputted tilt angle and the positional plane; determine implant orientation measurements using the respective optical measurements from the surgical tool as it is tracked during an implant placement procedure, referencing the implant orientation measurements relative to the second reference plane; and display, in a graphical user interface, the implant orientation measurements relative to the second reference plane.

There is disclosed herein a computer implemented method to provide intra-operative anatomic measurements to guide placement of an implant, the method comprising the steps of: registering, by at least one processor of an intra-operative computing unit, a first reference plane for an anatomy of a patient in a defined coordinate system using image data of a probe tool, where the probe tool points to at least three reference locations on the anatomy to define the first reference plane, the image data received from an optical sensor configured to generate and communicate image data of respective targets attached to the probe tool and a surgical tool to track the probe tool and surgical tool during an implant placement procedure; receiving optionally, by the at least one processor, an inputted tilt angle of the anatomy of the patient relative to a second plane within the defined coordinate system; generating, if the inputted tilt angle is received, by the at least one processor, a second reference plane for the anatomy of the patient using the inputted tilt angle and the first reference plane; determining, by the at least one processor, implant orientation measurements using the respective image data from the surgical tool as it is tracked during the implant placement procedure, referencing the implant orientation measurements relative to the second reference plane; and displaying, by the at least one processor, in a graphical user interface, the implant orientation measurements relative to the second reference plane.

The method is further configured to perform the steps of: receiving, by the at least one processor, inclination measurements from an inclination sensor configured to generate and communicate inclination measurements to track the anatomy of the patient during the implant placement procedure where changes in inclination of the inclination sensor correspond to changes in inclination of the anatomy of the patient and registering, by the at least one processor, a positional plane for the anatomy of the patient in the defined coordinate system using the inclination measurements, equating the positional plane to a horizontal plane within the defined coordinate system.

The method is further configured to perform the steps of: calculating and displaying, by the at least one processor, a tilt angle of the anatomy of the patient relative to the horizontal plane using the first reference plane and the positional plane. The second plane is a standing coronal plane. The anatomy of the patient is a pelvis. The inputted tilt angle is a pelvic tilt determined from a pre-operative medical image of the pelvis. The first reference plane is the anterior pelvic plane determined when the patient is in a supine position. The method further provides a graphical user interface to receive and display the inputted tilt angle. The method further configured to perform the step of receiving, by the at least one processor, the inputted tilt angle from an image analyzer communicatively connected to the at least one processor.

BRIEF DESCRIPTION OF DRAWINGS

Embodiments disclosed herein will be more fully understood from the detailed description and the corresponding drawings, which form a part of this application, and in which.

Figure 1:
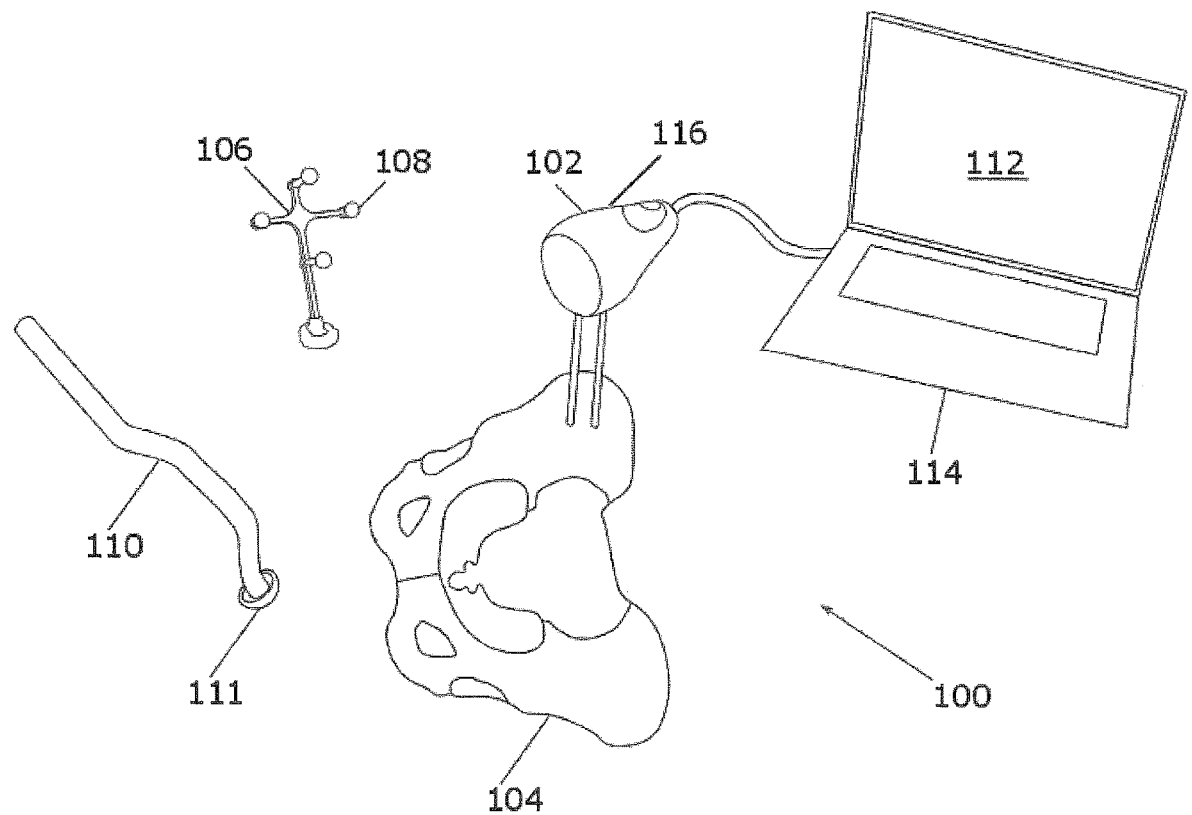
FIG. 1 depicts an electronic guidance system, in accordance with one example, for surgical navigation during a THA.

It will be appreciated that for simplicity and clarity of illustration, elements shown in the figures have not necessarily been drawn to scale. For example, the dimensions of some of the elements may be exaggerated relative to other elements for clarity.

DETAILED DESCRIPTION

THA begins by positioning the patient on an operating table in a known position and/or orientation with respect to a landmark. The patient may be positioned lateral decubitus or supine depending on the surgical approach. A surgeon then creates an incision near the hip joint. The surgical procedure usually begins by dislocating the hip joint, and preparing the acetabulum in order to subsequently insert an acetabular cup implant. A trial cup is usually inserted first, in order to check the proper alignment and fit of the cup within the acetabulum. The surgeon may conduct several trials before deciding on a final acetabular implant.

Minimally invasive approaches to THA procedures, including but not limited to the direct anterior approach, present unique challenges when applying surgical guidance technology to assist in the placement of prosthetic implants. Such problems include, but are not limited to, determining a center of rotation of the hip joint, both prior to dislocation of the hip joint and following placement of the prosthetic implant, through a minimally invasive incision that is typically only a few centimeters wide; and utilizing information about the orientation of a pelvis of the patient while standing (as obtained from pre-operative scanning or other known methods in the art) during the process of placing an acetabular implant during THA as the patient lies supine, etc.

The problems presented herein are explained in the context of the direct anterior approach to total hip arthroplasty, but can also extend to additional approaches to hip surgery, or other surgical procedures. A major difference between the direct anterior approach to THA and other approaches (e.g. posterior approach) is that the patient is positioned supine during the procedure.

Systems, methods and devices are presented herein pertaining to calculating a center of rotation of the hip, calculating implant orientation measurements of prosthetic implants to compensate for pelvic tilt of the pelvis, and calculating leg length and offset parameters during a THA. The exemplary variations in this specification refer to use of an electronic guidance system in THA. However, a person skilled in the art will realize that the specification is applicable to other forms of surgery and is not meant to be limited to THA (for example, calculation of a center of rotation of a shoulder joint). It is further understood that various methods described for performance by an intra-operative computing unit such as navigational surgery may be implemented in software such as instructions and data to configure at least one processing unit to perform the method. The instructions and data may be stored in a device such as a memory (RAM, ROM, flash drive, etc.) or other non-transitory storage device (e.g.: magnetic, optical, or other disk or storage medium).

Several systems, methods and devices will be described below as embodiments. The scope of the claims should not be limited by the embodiments set forth in the examples, but should be given the broadest interpretation consistent with the description as a whole.

In many surgical procedures, electronic guidance systems (also known as localization, navigation or computer assistance) provide the surgeon with intra-operative implant orientation measurements to precisely guide the placement of implants and assist in implant selection. An exemplary electronic guidance system applied to hip surgery is shown in FIG. 1. A sensor apparatus comprising an optical sensor 102 and is attached to a bone of the patient 104. In FIG. 1, this bone is a pelvis. The optical sensor 102 is configured to detect a target 106 comprising markers 108, such markers having a positional relationship with respect to a base of the target 108. The target 108 may be attached to an instrument 110 (for example, an impactor or an inserter) or to a femur of the patient. The geometric information regarding this positional relationship is used to provide intra-operative surgical navigation through a graphical user interface (GUI) 112 on a computing unit 114. During an implant procedure, the optical sensor may be attached to a patient's bone as in the present example or to another surface (not shown), for example a fixed or steady surface such as an operating table. A target can be attached to various objects, including bones and instruments, and can be tracked by the optical sensor. The optical sensor is in communication with a computing or processing unit to provide image data and the computing unit processes the image data to calculate the pose (position and orientation) of the target. In this example, an acetabular implant 111 (also referred to as a cup) is shown attached to its insertion tool, an acetabular impactor. The system includes a display to convey information such as measurement information to a user. A surgeon is a user of such a system and the terms—surgeon and user—are used interchangeably in this specification but are intended to cover surgical staff. This exemplary system relies on an optical modality of communication between the optical sensor and target. However, this specification is not to be limited by modality and includes other known modalities in the art, for example, inertial, electromagnetic.

The sensor apparatus may further comprise an inclination sensor 116 (for example, an accelerometer) that provides inclination measurements. In conjunction with the optical measurements, these inclination measurements may enhance the accuracy of measurements provided for surgical navigation. If an inclination sensor 116 is used along with an optical sensor 102 (housed in the same electronic unit as shown in FIG. 1 or otherwise), both sensors may be co-registered in order to correlate the measurements captured by each sensor and provide navigation data to the user in the same coordinate system.

In examples presented in this specification, as mentioned, the optical sensor is attached to a bone of the anatomy of the patient or a steady surface such as an operating table. A target, detectable by the optical sensor in up to six degrees of freedom, is located on an object being tracked, such as another bone of the anatomy of the patient, a tool, a prosthesis, etc. However, in general, the locations of the optical sensor and target can be reversed without compromising functionality (e.g. fixing the target on the bone or a steady surface and attaching the optical sensor to the object to be tracked), and this specification should be interpreted accordingly.

Figure 2:
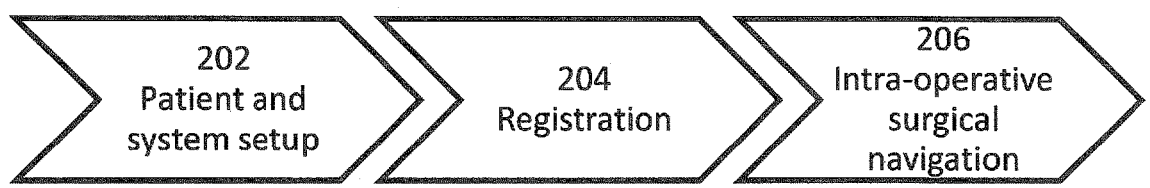
FIG. 2 depicts a typical workflow of the electronic guidance system of FIG. 1.

Reference is now made to FIG. 2 that depicts a workflow of an electronic guidance system 100 used for surgical navigation. This method does not describe surgical steps such as dislocation of the hip joint, resection of the femur, reaming of the acetabulum etc. but instead refers to steps pertaining to the electronic guidance system. In step 202, the electronic system and its components are set up as a patient is positioned for surgery on an operating table. In step 204, the electronic guidance system defines a coordinate system for the anatomy in a step commonly known in the art as registration. The electronic guidance system determines a spatial location of the patient's anatomy with respect to a defined coordinate system of the sensor apparatus in a step commonly known in the art as registration. To register, in the context of this specification, refers to a determination of a spatial location of a point or plane or a coordinate system of an object in a defined coordinate system of the electronic guidance system. In step 206, measurements calculated by the electronic guidance system are then provided intra-operatively with respect to this point or plane or coordinate system of the object determined during registration.

Surgical instruments that may be used with the system to perform these steps include tools such as, a liner impactor, a cup impactor, a reamer for the acetabulum, a probe, a digitizer tool, etc. Different instruments may also need to be calibrated i.e. the electronic guidance system determines the shape and geometrical features of the tool with respect to a target affixed thereto, before being able to provide measurements to the user. In one example, calibration may be performed pre-operatively and definitions of the shape and geometrical features of the various tools (with respect to the tool's target) may be pre-stored into the computing unit Calibration of some surgical instruments may involve the determination of a center of rotation of the tool about its end effector e.g. a probe tool with a sharp tip at a distal end would be calibrated when the spatial location of the tip is determined with respect to a target affixed to the probe; an impactor comprising a shaft would be calibrated when the spatial location of a distal end of the shaft is determined with respect to a target affixed to the impactor.

I. Determining Hip Center of Rotation Through a Minimally Invasive Incision

In THA procedures, a center of rotation (CoR) of the hip joint is a valuable measurement. This is a point about which the head of the femur articulates within the acetabulum. In the context of this specification, "articulate" is a verb referring to the movement of an object within a ball and socket type joint of a patient, the movement being constrained by the joint. In particular, the joint may be a hip joint, and the object may be a femur or a surgical instrument. The movement of the object within the hip joint is constrained such that the object is only permitted to move about the pivot point of the hip (i.e. the hip CoR).

Determining hip CoR is important, as it may provide or enable useful and accurate measurements during a navigated THA. For example, a post-reduction CoR may be used to enhance leg position measurements (e.g. leg length change, offset change) as measured by an electronic guidance system for surgical navigation. The post-reduction CoR may enable a post-reduction leg position measurement to be more accurate by virtually re-aligning the leg about the hip center of rotation to ensure that the pre-dislocation and post-reduction leg positions are compared with respect to the same leg orientation. This eliminates the requirement to re-orient the patient's leg back to its baseline position in order to get accurate measurements. In another example, determining both the pre-dislocation and post-reduction hip CoR enables a positional change in hip CoR to be calculated (e.g. by a computing unit in communication with the optical sensor) and displayed to a user.

In the posterior and lateral approach to THA, a large incision permits the removable mounting of a target to the femur within the primary surgical incision. For additional details, see U.S. Pat. No. 9,247,998 which is incorporated herein by reference. When an optical sensor is used to track the pose of the target as the femur is articulated in the acetabulum, the CoR of the hip can be calculated.

In the direct anterior approach to THA, a much smaller incision restricts the ability to mount a removable target within the primary surgical incision (for example, soft tissues may prevent the target from being able to be attached to the femur). The patient is supine in the direct anterior approach. Fast and sufficiently accurate solutions for determining the hip CoR during the direct anterior approach, as well as other minimally invasive approaches to THA are desired to aid surgeons in treating their patients.

Figure 3A:
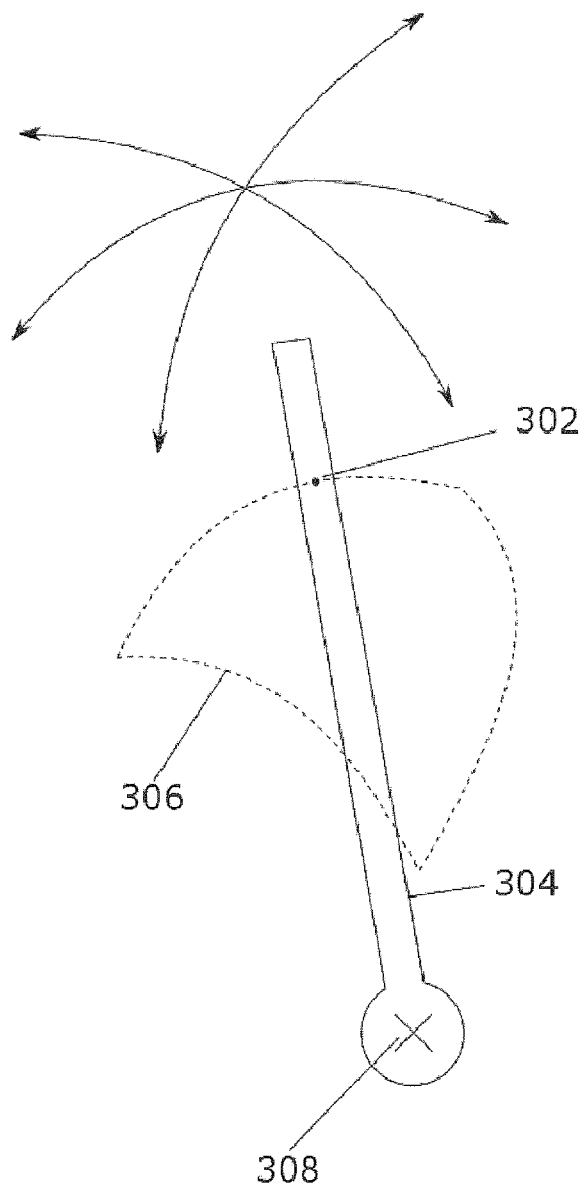
FIG. 3a depicts a rotation of an object articulated about a single point to determine a center of rotation of the object.
Figure 3B:
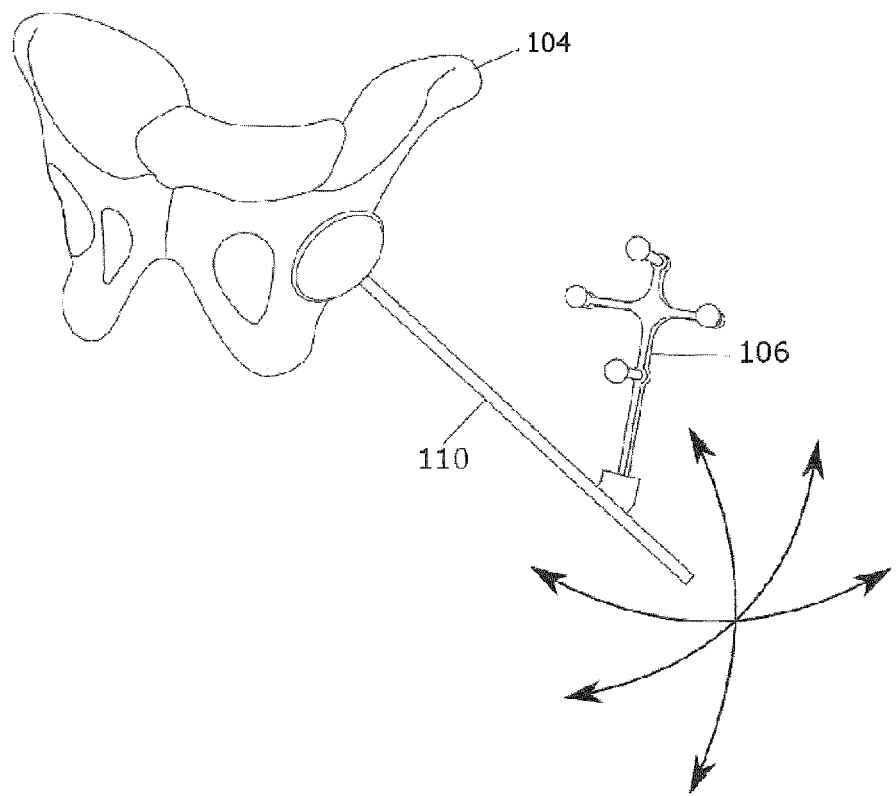
FIG. 3b depicts an articulation of a surgical tool in an acetabulum, which articulation may be tracked by the system of FIG. 1 to calculate a center of rotation of the hip joint.

When an object is articulated, or rotated, about a single point, that point is the centre of rotation (CoR). The poses of the object (or of the target attached to the object) during articulation may be used to calculate the CoR. FIG. 3a shows the manner in which the CoR can be located, particularly for rigid objects. During articulation, a fixed point 302 on the articulating object 304 will follow the profile of a spherical surface 306. As the object 304 is rigid, fixed point 302 maintains a constant distance from the CoR of the object as the object is articulated. Determining the centre of this spherical surface will provide the point about which the object is articulating, its centre of rotation 308. This may be accomplished by a computing unit executing instructions to perform center of rotation calculations based on the position and orientation of the object during articulation. With reference to the previously described surgical localization or electronic guidance system and illustrated in FIG. 3b: the articulating object is anything that can articulate within the acetabulum of the pelvis 104, such as a femur or surgical tool 110; the fixed point 302 on the articulating object 304 is a target 106 (the target being trackable by the optical sensor 102 of the electronic guidance system 100) and the point of articulation is the hip CoR 308.

The optical sensor of the electronic guidance system is used to measure the pose of the target while the target is attached to the object and the object is articulated about the hip CoR. A computing unit may process the collection of target poses by using each measured pose to perform an optimization routine that fits a sphere to the target's various positions throughout the articulation and calculate the center of the sphere in a defined coordinate system.

As described above, various instruments may need to be calibrated for use in surgical navigation. One such instrument includes a probe tool with a shaft and a tip (at a distal end). During the calibration of a probe to be used during surgery, a CoR calculation is performed by the computing unit in order to determine a geometrical relationship of the target (that is attached to the probe) and the effector of the probe i.e. its tip, by articulating the probe at a fixed point of rotation. The computing unit comprises a display screen that offers guidance to a user as the user is performing the articulation. The computing unit may execute instructions to detect errors as each pose of the target is captured to determine whether the pose is valid or not. The "expected" range of motion, in this case, is a spherical trajectory of poses and may be obtained by comparing each pose to a set of previously captured poses to verify that the pose matches an expected spherical profile. An invalid pose may be captured when the user's hand slips or moves such that the same point is not in contact with the tip of the probe during the articulation. The instructions may execute such that an articulation will not complete until a minimum number of valid poses are captured or will restart when slippage is detected. Feedback to the user may be provided in the form of a counter, or a progress bar indicating the capture of valid poses displayed on a display screen such that a user is unable to bypass this step until an appropriate set and/or number of poses is captured by the system.

Figure 4:
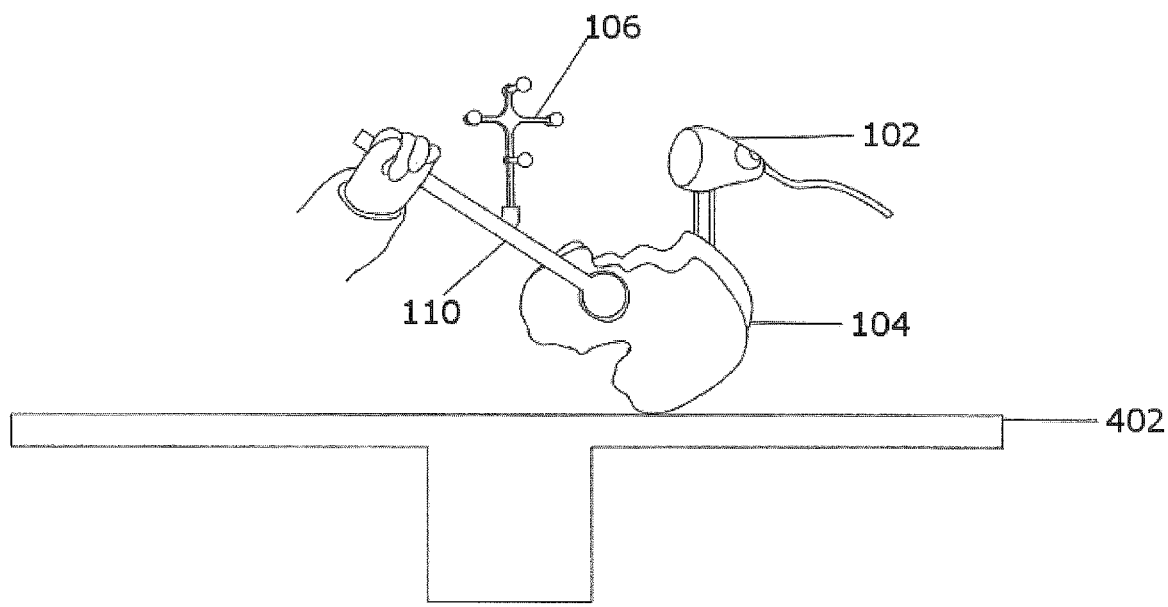
FIG. 4 shows a side view of selected components of an exemplary electronic guidance system for use during a procedure using the direct anterior approach in THA as the patient lies supine on an operating table.

As previously described, the method of tracking the pose of a target removably mounted to the femur within the primary surgical incision is not practical in the direct anterior approach to THA. Instead of articulating the femur within the acetabulum, the method described herein includes using an existing surgical tool to locate the hip CoR. The system for performing such method is shown in FIG. 4. In the direct anterior approach to THA, the patient's pelvis 104 is positioned supine on an operating table 402. The acetabulum is exposed through the primary surgical incision. Various surgical tools 110 that are handheld by a user may be used to mate with the acetabulum. These tools may be tracked relative to the pelvis, and articulated such that a CoR may be computed. The target 106 of the electronic guidance system is capable of being removably (or fixedly) attached to the shaft of the existing surgical tool 110. Poses of the target are captured as the tool is articulated about a single point. The optical sensor 102 of the electronic guidance system is capable of measuring the pose of the target as the tool is articulated within the acetabulum. The instructions executing on the computing unit use the pose measurements to calculate the point of articulation of the tool, as described above. The point of articulation of the tool corresponds to the centre of rotation of the hip joint.

The tool described above comprises: a rigid shaft to which the target can be removably mounted; and a spherical surface about which to articulate the tool within the acetabulum. The rounded surface can either be part of the tool itself or a separate object to which the tool can be rigidly attached. The acetabulum can be either the native acetabulum prior to implant placement or the acetabular component of the implant following insertion of the implant. The tool may be an existing surgical tool included in the standard set of surgical tools used in THA procedures.

Figure 5A:
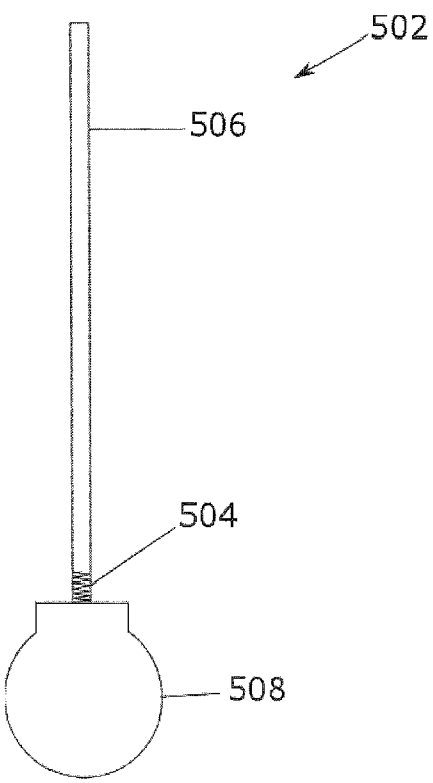
FIG. 5a shows a side view of a corkscrew tool comprising a threaded feature being inserted into a resected femoral head.

In order to provide the surgeon with the change in the hip CoR during a THA, the pre-operative, or native, hip CoR must be calculated. A common practice in the direct anterior approach to THA is to perform the femoral neck cut in-situ i.e. to resect the head of the femur at the femoral neck prior to dislocating the head from the acetabulum. As shown in FIG. 5a, a surgical tool 502 comprising a threaded feature 504 on one end of a long shaft 506 is then inserted into the head of the femur 508. This tool is herein referred to as the corkscrew tool. The corkscrew tool is a standard tool included in instrument sets used in THA procedures.

Figure 5B:
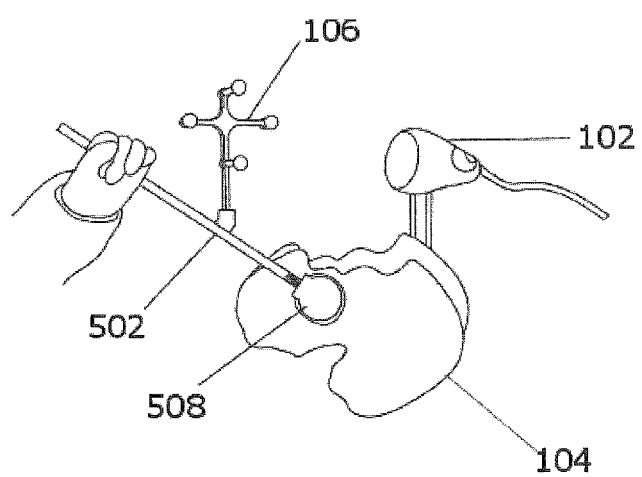
FIG. 5b shows a side view similar to FIG. 4 for determining a pre-operative hip center of rotation using the corkscrew tool.

Reference is now made to FIG. 5b. The shaft of the corkscrew tool 502 is used to articulate the femoral head 508 in the acetabulum to remove the femoral head from the fossa. This articulation of the femoral head occurs about the native hip CoR, despite the fact that the femoral head is no longer attached to the femur. As described in the preceding paragraphs, the corkscrew tool is articulated about the native hip center of rotation. The rounded surface about which the tool articulates within the acetabulum is the resected femoral head. To calculate the native hip CoR, the target 106 is mounted to the shaft of the corkscrew tool 502. The optical sensor 102 collects image data that represent the poses of the target during articulation within the acetabulum and the computing unit executes instructions to determine the native hip CoR using the poses, as described previously.

Alternatively, a probe tool or a custom tool with a sharp tip on a distal end and a base to attach a target on a proximal end, etc. may be used instead of a corkscrew tool. A user may hammer in the sharp tip by impacting an opposite end of the probe tool or custom tool into the femoral head and be able to perform the articulation in a similar fashion as described for the corkscrew tool.

Figure 6:
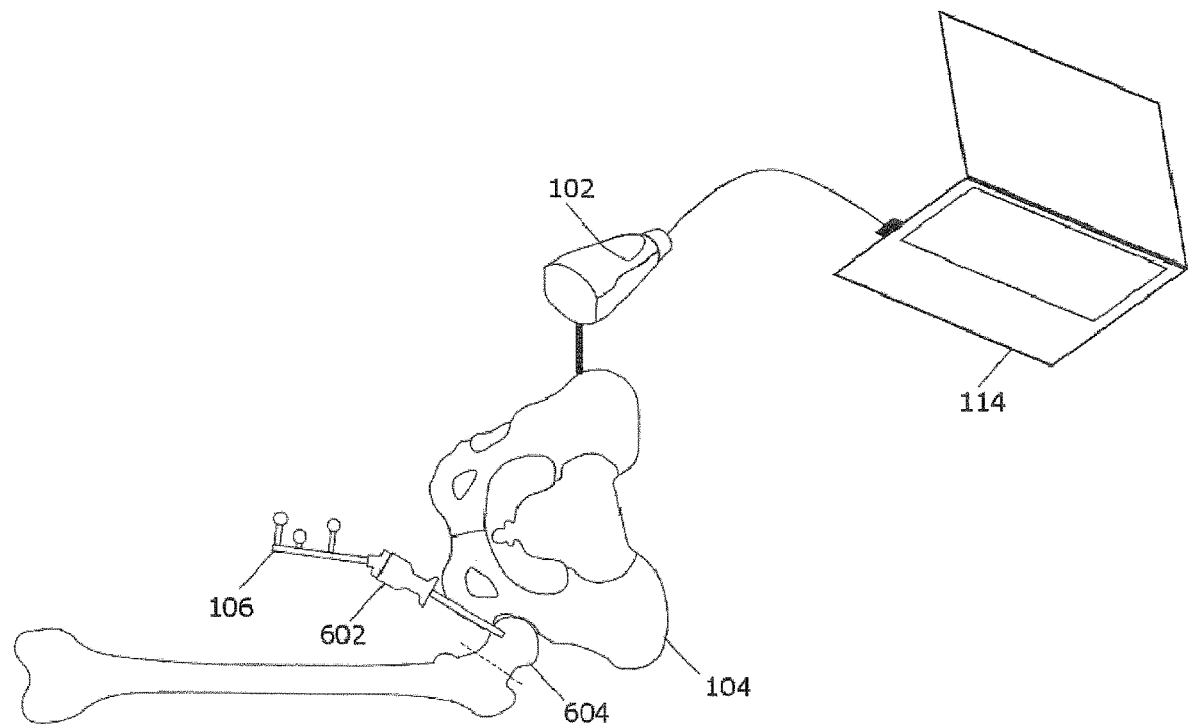
FIG. 6 shows a top view of an example electronic guidance system for determining a pre-operative hip center of rotation before resection of a femoral head.

It may also be possible to perform such articulation without resecting the femoral head. Reference is now made to FIG. 6 that depicts an electronic guidance system 100 where a tool 602 with a sharp tip is hammered in the femoral head 604 before the joint is dislocated. A target 106 is attached to the tool 602 and is trackable by an optical sensor 102, the optical sensor being attached to the pelvis 104. Articulation of the femur with the tool hammered in as shown allows a calculation of a center of rotation of the hip joint by a computing unit 114 that is in communication with the optical sensor 102.

The hip center of rotation (CoR) following insertion of the acetabular implant, i.e. the post-operative hip CoR, is used to provide the surgeon with the change in the hip CoR as well as calculate accurate leg length measurements. During THA procedures, the prosthetic acetabular cup is inserted and secured into the acetabulum. A prosthetic implant liner is then positioned in the cup and a liner impactor is used to press the liner into the cup such that it remains seated in the cup. A liner impactor is an existing tool in instrument sets used in THA procedures. The liner impactor consists of a rigid shaft and a removable spherical ball attached to a distal end of the shaft that fits inside the curvature of the implant liner (i.e., the spherical ball and the implant liner have mating spherical surfaces of the same diameter). Using the liner impactor instead of any other tool that has a spherical tip is advantageous because the liner impactor is designed to mate with the liner without causing any damage (e.g. scratches) that may compromise the liner's articulating surface. Various sizes of the ball component are available in instrument sets utilized during THA and the available sizes correspond to the sizes of implant liners available. This is advantageous as a user to already have access to an appropriately sized ball component for all procedures.

Figure 7:
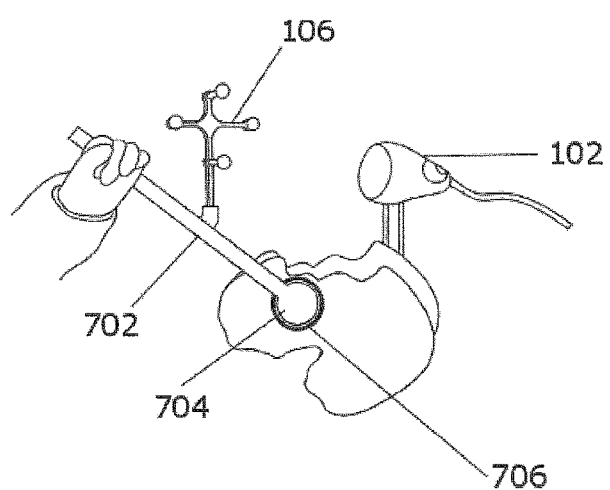
FIG. 7 shows a side view of selected components of an electronic guidance system for determining a post-operative hip center of rotation using a liner impactor tool, as an example for clarity.

Reference is now made to FIG. 7. In this exemplary system showing select components, a liner impactor 702 is articulated about the rounded surface of the smooth spherical ball 704 that is attached to the distal end of the liner impactor. In some existing products, the acetabular cup impactor is configured to receive a spherical attachment so that it may be used as the liner impactor. To calculate the post-operative hip CoR, the target 106 is mounted to the shaft of the liner impactor 702 to maintain a fixed relationship between the target and the shaft. As the liner impactor is articulated within the implant liner 706, the optical sensor 102 measures the pose of the target 108 and instructions executing on the computing unit use the poses to determine the post-operative hip CoR, as described previously.

Figure 8A:
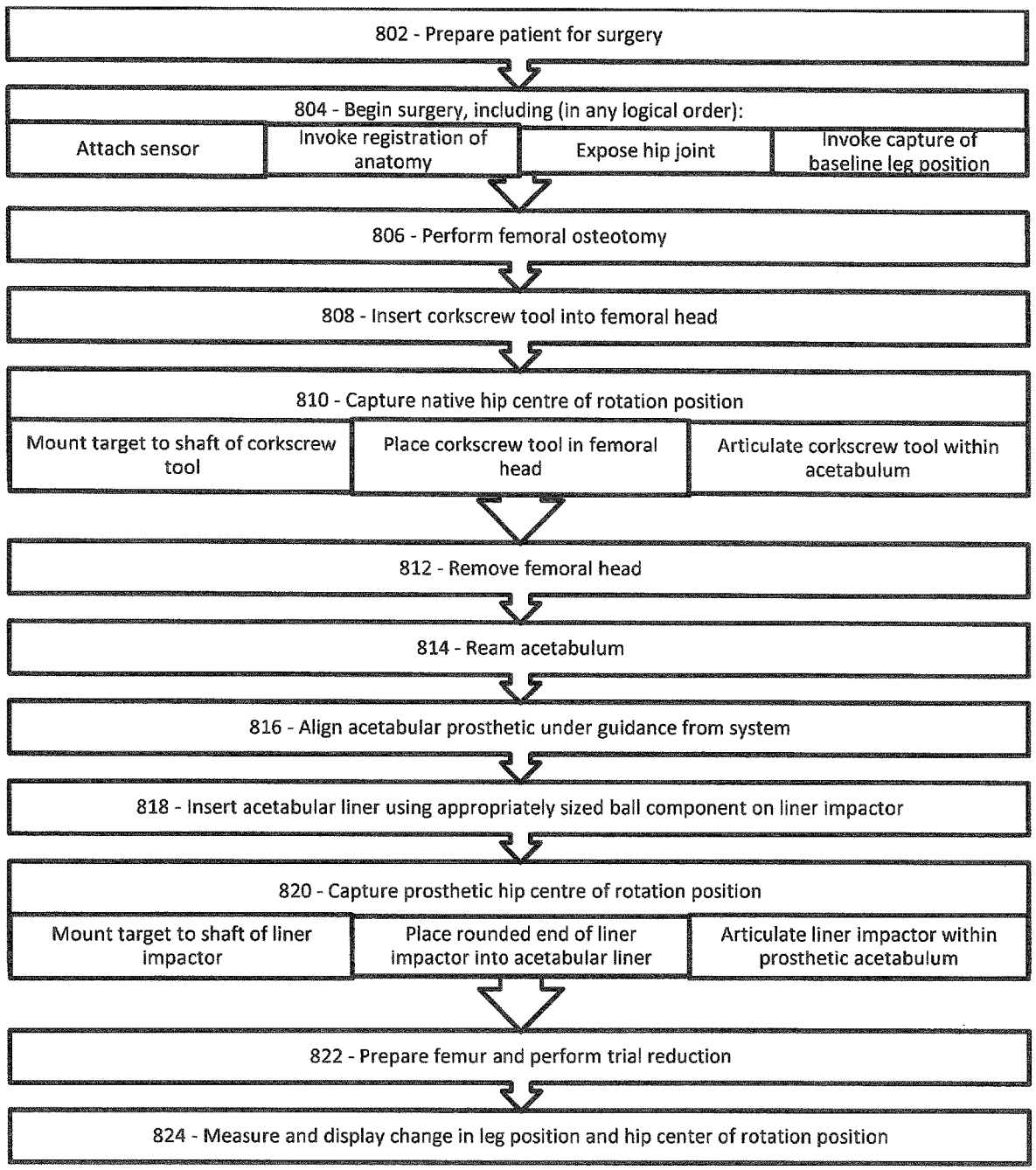
FIG. 8a depicts a method of performing THA using the direct anterior approach including invoking a calculation of pre and post-operative hip center of rotation, as an example for clarity.

Reference is now made to FIG. 8a. Various methods for calculating the hip CoR using a surgical tool are presented herein. The following provides an exemplary method 800 illustrating the direct anterior approach to THA as performed by a surgeon.

1. At step 802, prepare patient for surgery.
2. At step 804, begin surgery, including (in any logical order):
   a. Attach sensor apparatus.
   b. Invoke registration of the anatomy by the computing unit.
   c. Expose hip joint.
   d. Invoke capturing of a baseline leg position measurement by the computing unit.
3. At step 806, perform femoral osteotomy.
4. At step 808, insert corkscrew tool into femoral head.
5. At step 810, invoke capture native hip center of rotation by the computing unit.
   a. Mount target to shaft of corkscrew tool.
   b. Place corkscrew tool in the femoral head.
   c. Articulate corkscrew tool within the native acetabulum about the femoral head and invoke capture of poses of the target.
6. At step 812, remove femoral head.
7. At step 814, ream acetabulum.
8. At step 816, align acetabular implant under guidance from system.
9. At step 818, insert acetabular liner using appropriately sized ball component on liner impactor.
10. At step 820, invoke capture of prosthetic hip center of rotation by the computing unit.
    a. Mount target to shaft of liner impactor.
    b. Place rounded end of liner impactor into acetabular liner, the liner being inserted in the acetabular implant.
    c. Articulate liner impactor about its rounded end and invoke capture of poses of the target.
11. At step 822, prepare femur and perform trial reduction.
12. At step 824, invoke capture of final leg position, measurement of change in leg position as against the baseline and display change in leg position and change in hip centre of rotation by the computing unit.

Figure 8B:
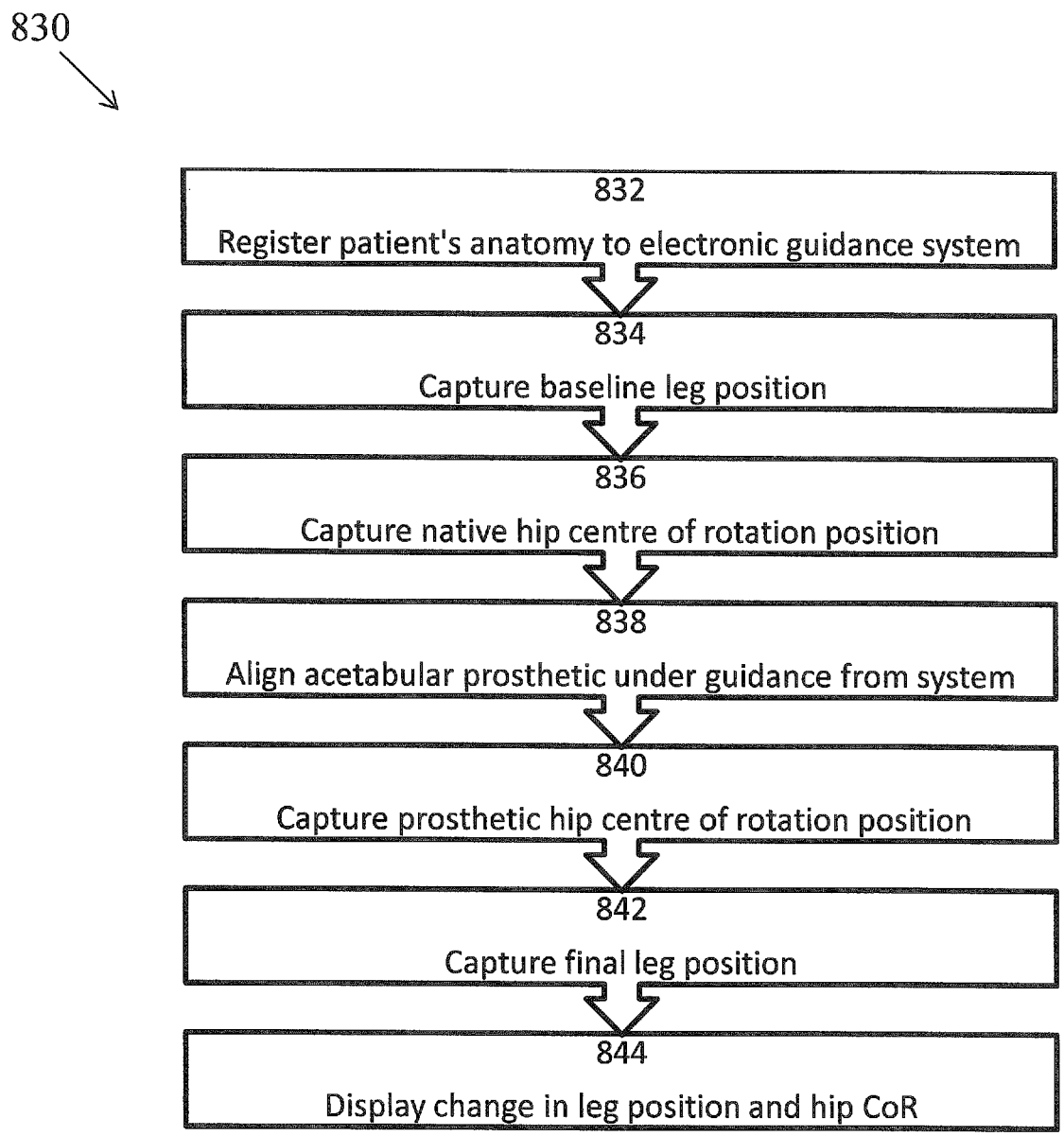
FIG. 8b depicts a computer implemented method including steps of the electronic guidance system of FIG. 1 to calculate a pre- and post-operative hip center of rotation, as an example for clarity.

Reference is now made to FIG. 8b which describes a corresponding computer implemented method 830.
1. At step 832, register the patient's anatomy to the electronic guidance system.
2. At step 834, capture a baseline leg position measurement.
3. At step 836, capture a native hip center of rotation.
4. At step 838, align acetabular implant under guidance from system.
5. At step 840, capture of prosthetic hip center of rotation.
6. At step 842, capture of final leg position.
7. At step 844, display change in leg position and change in hip centre of rotation.

Several devices are described herein to calculate a center of rotation of a hip joint. The variations described are not meant to be limited and independent features of each variation may be combined. Each variation describes specific advantages which may be combined into a preferred embodiment.

Figure 9A:
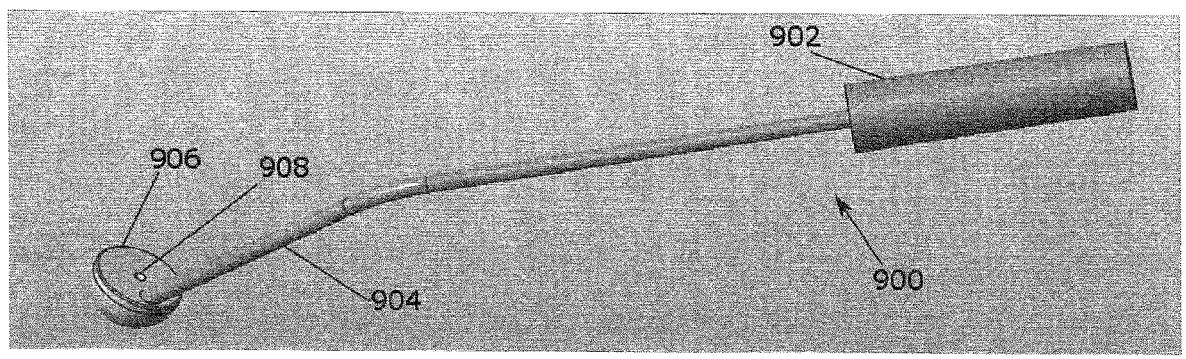
FIGS. 9a, 9b, 9c and 9d show tools and attachments that allow calculation of a center of rotation of a joint.

Reference is now made to FIG. 9a. Disclosed herein is device 900 comprising a handle 902 to allow for access in to a miniature surgical wound; a shaft 904 that is offset from the handle 902. The device 900 is configured to allow a user to grasp the handle 902 and a distal end of the shaft 904 is configured to mate with an attachment. Alternatively, the shaft and the attachment may form a conjoined piece. The attachment may be a spherical attachment 906 that is available in different sizes to accommodate standard acetabular liners. This spherical attachment comprises a divot 908 located at a centre of the sphere allowing a user to contact a probe tool in the divot while the device 900 is held within a spherical cavity.

In operation, the probe tool further comprises a target (not shown) (fixedly or removably attached to the probe tool) that provides image data to allow the calculation of a pose of the target. The pose can be used to determine the center of the spherical attachment and hence, the center of rotation of the hip joint, provided the target is detected by the optical sensor of the electronic guidance system. The divot may be designed to allow a tip of the probe tool to firmly be placed within it without slippage. The spherical attachment does not require an articulation of the device within the acetabulum and allows a single capture of the pose of the target attached to the probe tool to allow the instructions executing on the computing unit to calculate a center of rotation.

Figure 9B:
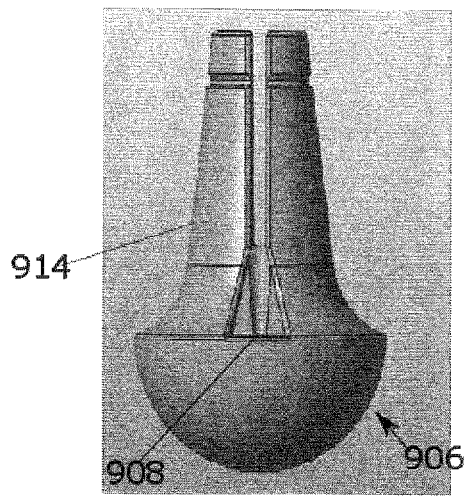
Figure 9C:
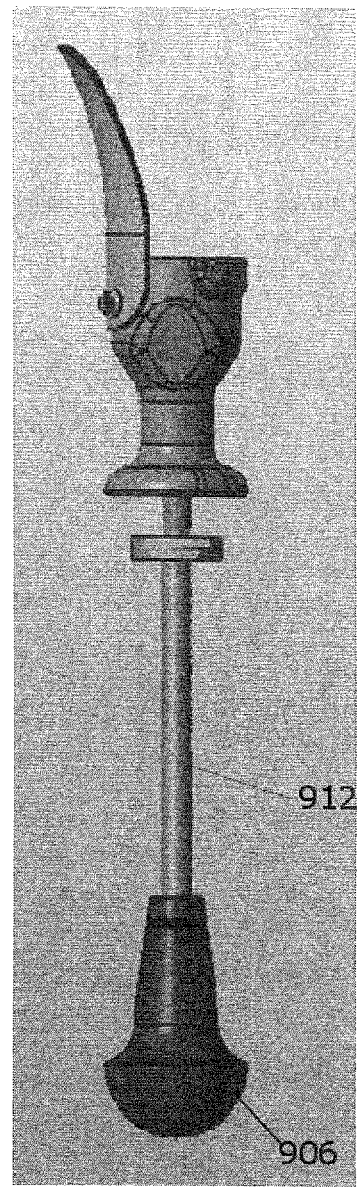

Alternatively, a variation of the spherical attachment 906, may be used during articulation and may be configured to be attached to the distal end of the probe tool, the end comprising a tip. Reference is now made to FIG. 9b illustrating an enlarged view of the spherical attachment 906 and FIG. 9c showing the use of the spherical attachment 906 comprising a divot 908, with a probe tool 912 comprising a tip (not shown). The spherical attachment may be configured to provide feedback (tactile, audible or visual) to a user to confirm that the tip of the probe tool 912 has been seated accurately in the center of the attachment. As illustrated, a hollow cylinder 914 allows a probe tool to slide in to the spherical attachment 906 to engage with the divot 908. The hollow cylinder 914 may be configured to allow a user to view the tip of the probe tool 912 and visually verify that the tip of the probe tool 912 is engaged with the divot 908 as illustrated in FIG. 9b. In operation, once the probe tool 912 is placed within the spherical attachment 906, a single pose of the target may allow instructions executing on the computing unit to capture a center of rotation of the acetabular liner within which the spherical attachment is placed.

Figure 9D:
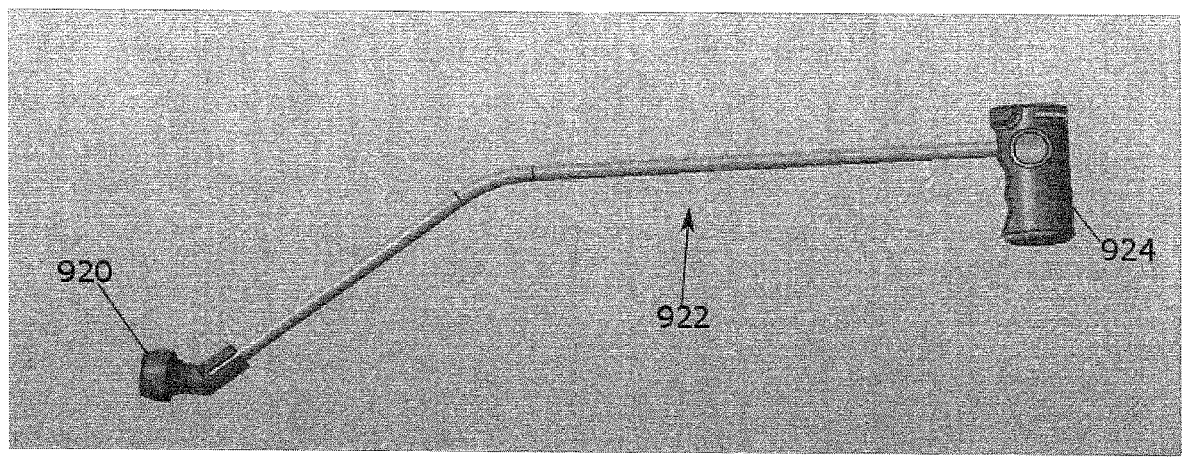

Reference is now made to FIG. 9d. A flat disc attachment 920 at a distal end of a tool 922 may allow a single attachment to be used with various sizes of the acetabular liner. The tool 922 may have a handle 924 that can easily be grasped by a user. In operation, a user may be required to articulate the tool with the flat disc attachment 920 in contact with a spherical surface of the liner. When engaged, the flat disc attachment contacts the spherical surface of the liner along a circle. Poses of the target (not shown) (fixedly or removably attached to the tool 922) captured from such an articulation may allow the instructions executing on a computing unit to calculate a center of rotation of the acetabular liner. A vector orthogonal to the circular contact surface (when the flat disc is in contact with the spherical liner) passes through the center of the sphere of the liner. Multiple vectors obtained from the articulation allow the computing unit to calculate a point of intersection of all the vectors, which is the center of rotation of the spherical surface. This attachment has the advantage of allowing one size to be used with multiple liners.

While the tools identified herein as capable of being used to calculated the hip CoR through a minimally invasive incision include the corkscrew tool and liner impactor, there are other existing surgical tools to which the target can be removably mounted to provide a manner of determining hip CoR both prior to and following implant placement. Methods to calculate the hip CoR have been described herein in relation to the direct anterior approach to THA. There are various clinical applications of this method, including but not limited to: other minimally invasive approaches to THA, such as the posterior-mini approach; and particularly difficult THA cases in which a target is unable to remain reliably fixed to the femur within the primary surgical incision as the femur is articulated about the femoral head within the acetabulum.

II. Determining Acetabular Cup Orientation Measurements

Pelvic tilt is the relative flexion or extension of the anterior pelvic plane relative to a patient's coronal plane. Pelvic tilt may be measured relative to a standing plane or a supine coronal plane. A patient may have anterior or posterior pelvic tilt.

A major determinant of the success of total hip arthroplasty is the orientation of the acetabular component of the implant. There is an accepted safe zone for this orientation that surgeons aim to achieve when placing the acetabular cup. Regardless of the accuracy of the method surgeons use when placing the acetabular implant in the desired orientation, the process is made challenging due to the multiple possibilities for anatomical planes to which these orientation measurements are referenced. A surgeon may choose one of a few different planes with respect to which an acetabular implant can be placed. This ambiguity leads different surgeons to reference different anatomical planes when placing the acetabular cup.

Some surgeons believe the orientation of the acetabular cup should be referenced to the patient's standing pelvic orientation rather than the orientation of the pelvis in a supine position. It is also widely known and accepted that the tilt of the pelvis relative to the coronal plane changes from standing to supine position. A pre-operative standing X-ray is captured with respect to the standing coronal plane. During THA using a direct anterior approach, a patient is lying supine and the electronic guidance system may allow the measurement of a supine coronal plane. The supine coronal plane corresponds to the plane of the operating table by positioning the patient parallel to the table due to careful positioning of the patient at the start of the procedure. However, when a patient is positioned supine, it is challenging for the surgeon to assess the orientation of the standing coronal plane. Surgeons aiming to orient the acetabular implant with respect to the standing coronal plane may have difficulty doing so when the patient is positioned supine, without the aid of any navigational or imaging devices.

A solution to provide surgeons with a standing coronal reference plane or a reference plane of choice for acetabular cup orientation measurements is desired to aid surgeons in treating their patients.

Figure 10A:
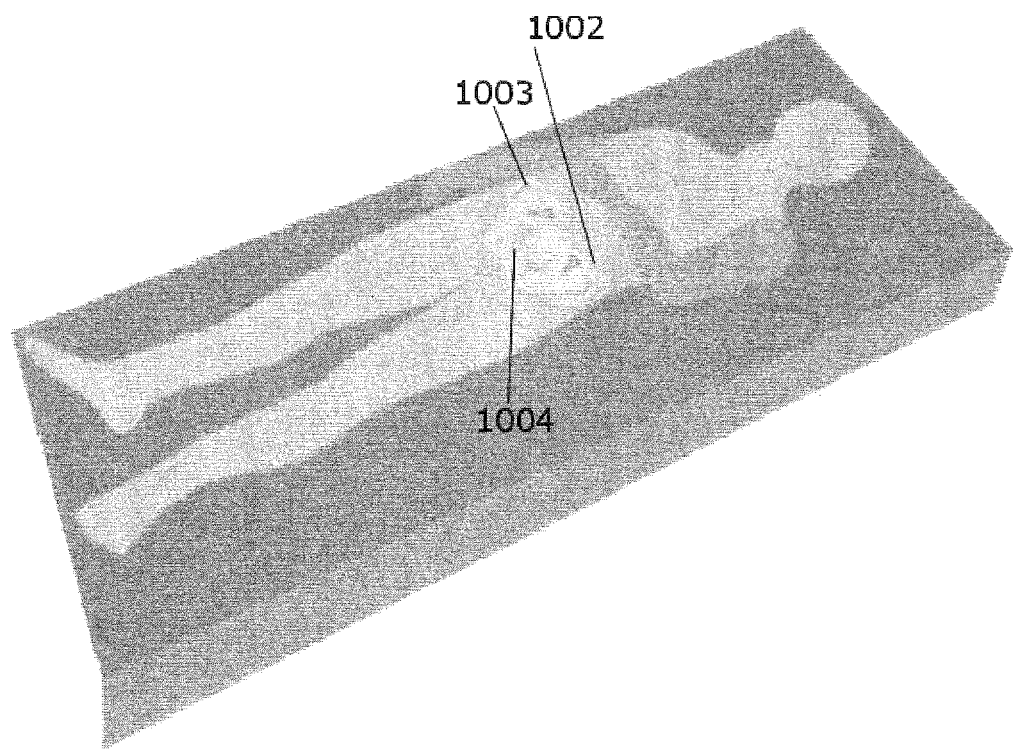
FIGS. 10a, 10b, 10c depict the different anatomical planes of the body that a surgeon may use for measurement of implant orientation measurements of an acetabular cup implant.
Figure 10B:
Figure 10C:
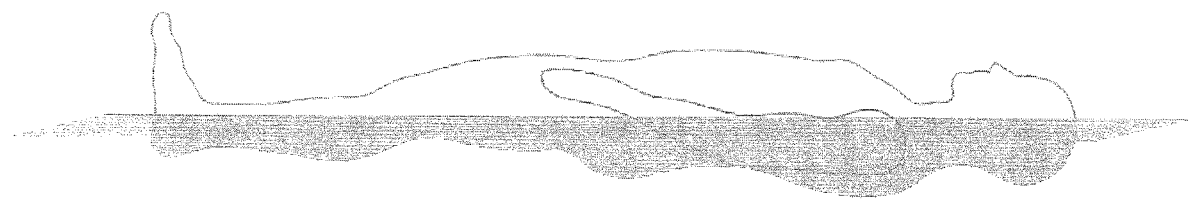

Reference is now made to FIGS. 10a, 10b and 10c that depict the generally accepted options of reference planes of the patient in THA. Each of these planes is described in further detail in the following paragraphs. These options include:

a. the patient's anatomical plane comprising the anterior pelvic plane obtaining by probing three bony landmarks on the patient's pelvis illustrated in FIG. 10a;

b. the plane with respect to which an intra-operative medical image of the patient's anatomy is captured;

c. the standing coronal plane of the patient with respect to which measurements are captured in a standard pre-operative lateral X-ray illustrated in FIG. 10b; and d. the supine coronal plane as the patient lies supine on an operating table illustrated in FIG. 10c.

The following paragraphs describe how each of the planes described above are captured in an electronic guidance system while allowing a user to modify the reference plane with respect to which cup orientation measurements are calculated and displayed.

Reference is now made to FIG. 10a. The positions of three points define a plane in a given coordinate system. It is widely accepted that three anatomical landmarks on the pelvis can be used to define the APP: the left anterior superior iliac spine (ASIS) 1002, right ASIS 1003 and pubic symphysis 1004. Locating these points within a coordinate system will enable a plane, corresponding to the APP to be defined in the same coordinate system.

In the direct anterior approach to THA, the patient is supine on the operating table. This position exposes anatomical references of the anterior pelvic plane, which are often registered by electronic guidance systems to generate a reference plane for acetabular implant orientation measurements. Typically, the anterior pelvic plane of a patient is registered by contacting at least three bony landmarks on the patient's anatomy. The three bony landmarks, in most cases, are the left ASIS, right ASIS and the pubic symphysis. The electronic guidance system comprises the optical sensor, the computing unit, and the target that is (removably or fixedly) attached to a probe tool such that the relationship between the tip of the probe tool and the target is known to the computing unit. To register the APP, the surgeon locates each anatomical landmark with the tip of the probe tool. Instructions executing on the computing unit use the pose of the target and the known relationship between the tip of the probe tool and the target to define the location of the anatomical landmark in a defined coordinate system that is used to reference measurements in the electronic guidance system. The GUI may instruct the surgeon of the order in which to register the anatomical landmarks. Once all three anatomical landmarks have been registered, the system generates the APP in the defined coordinate system.

Figure 10D:
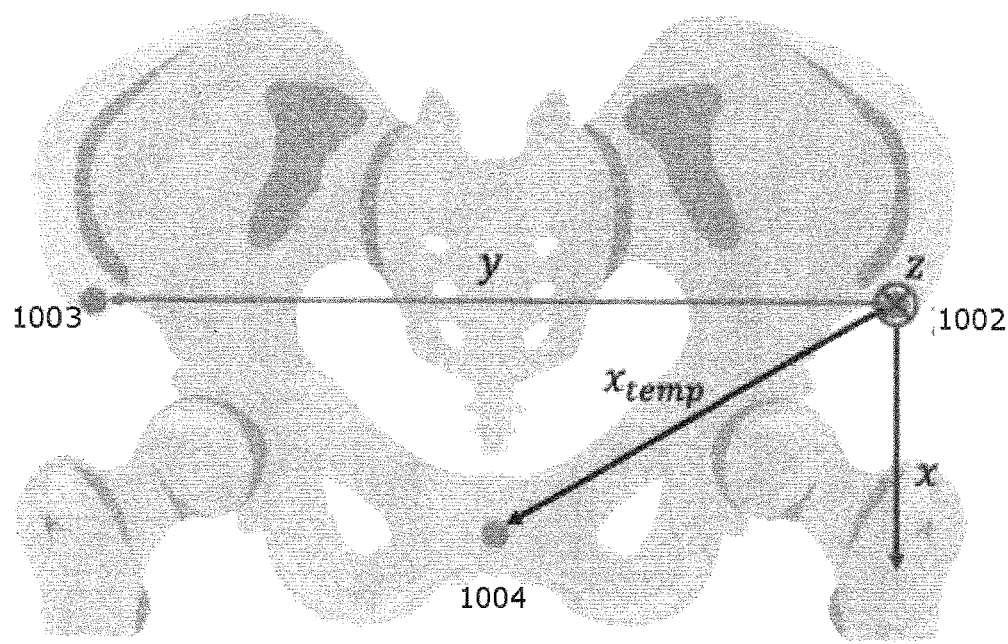
FIG. 10d shows a front view of a pelvis highlighting bony landmarks used for calculation of an anterior pelvic plane (APP)

Applying the following calculations in which $p_R$ and $p_L$ correspond to the right ASIS 1003 and left ASIS 1002 respectively and $p_{PS}$ corresponds to the pubic symphysis 1004, the computing unit can register the APP. FIG. 10d illustrates a front view of the pelvis showing vectors x, y, z and $x_{temp}$.

$$x_{temp} = p_{PS} - p_L$$

$$y = p_R - p_L$$

$$z = \hat{x}_{temp} \times \hat{y}$$

$$x = \hat{y} \times \hat{z}$$

$$R_{supine} = [\hat{x}\hat{y}\hat{z}]$$

A drawback of referencing the pubic symphysis in the previously described method is that this bony landmark is covered with soft tissue and when accessed by a surgeon, the soft tissue may interfere in the capture of an accurate landmark for calculation of the APP. This is particularly a problem for patients with a high body mass index (BMI) with significant soft tissue covering the pubic symphysis. The surgeon may probe an incorrect landmark due to the presence of the soft tissue. The two ASIS points typically are not subject to such inaccuracy as the depth of soft tissue is lesser than the pubic symphysis. In order to improve the accuracy of the APP captured by the electronic guidance system, information about the depth of the soft tissue over the pubic symphysis may be obtained from a pre-operative X-ray or medical image. The user/surgeon may then be expected to identify a point on a top surface of the skin above the pubic symphysis, instead of the bony landmark which corresponds to the pubic symphysis. The system may then compensate for the additional tissue using information provided by the X-ray or medical image and obtain a more accurate location of the pubic symphysis.

Figure 10E:
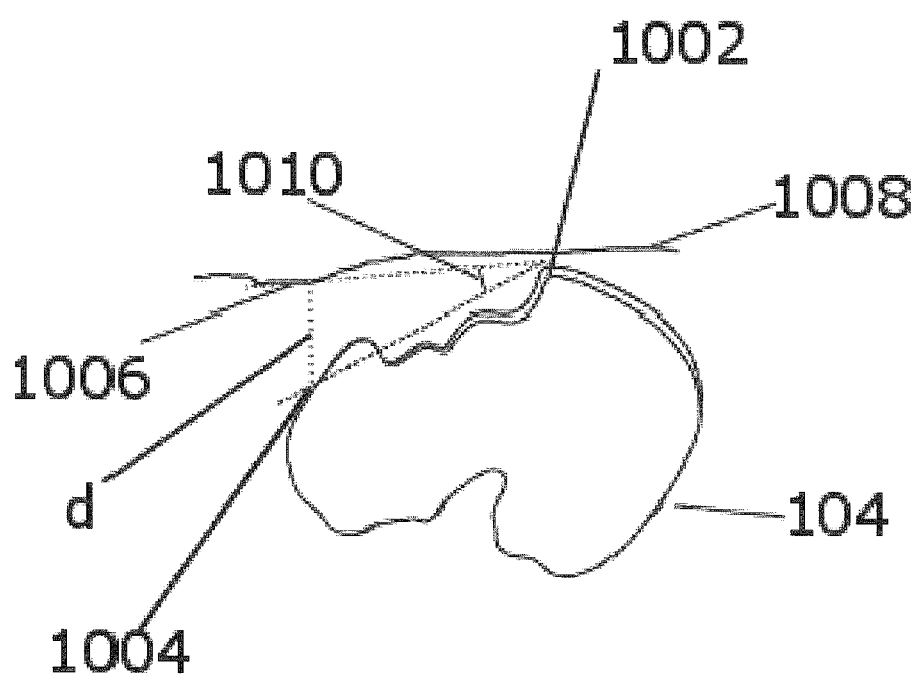
FIG. 10e shows a side view of an enlarged pelvis anatomy of a patient to highlight the calculation of a measurement between a pubic symphysis bony landmark and a surface of the skin above the landmark.

FIG. 10e illustrates an exploded side view of a pelvis 104 to further describe this scenario. The surgeon probes the left ASIS and the right ASIS (Figure only shows left ASIS 1002) and pubic symphysis 1004 to allow the computing unit to calculate the APP. The surgeon may probe a point 1006 on the skin 1008 (intentionally drawn unevenly). This point 1006 is above the pubic symphysis 1004. The system as described receives a measure of the thickness of soft tissue over the pubic symphysis 1004 that equates to a distance 'd' forming an angle 'ø' 1010. This distance may be obtained from a medical image or from a module executing instructions on the computing unit of the electronic guidance system and using the patient's BMI to estimate the distance 'd'. This angle 'e' is calculated using the distance 'd', as well as the distance between the ASIS points 1002 and 1003, and the probed point 1006 over the pubic symphysis 1004, using trigonometry. In the calculations described above, $p_{PS}$ is modified by "d" along a direction perpendicular to a plane formed by $p_R$, $p_L$ and $p_{PS}$ to allow a surgeon to probe a point on the surface of the skin instead of the pubic symphysis.

During THA, often a surgeon will capture an intra-operative medical image (for example, an Anterior-Posterior (AP) X-ray, an intra-operative C-arm shot, etc.) once the acetabular implant has been impacted in to the patient's pelvis. The medical image provides additional information about the seating of the acetabular implant in the patient's pelvis and allows the surgeon to verify the accuracy of the placement of the implant with respect to a pre-operative plan or pre-operative template. Multiple medical images are typically acquired, thus exposing the patient, the surgeon and the surgical staff to higher levels of radiation.

It may be possible to use an electronic guidance system along with a C-arm to verify acetabular implant orientation measurements. When a medical image is about to be captured by imaging equipment such as a C-arm, it may be possible to align or orient the equipment such that the reference plane of the medical image (e.g. the plane of the C-arm shot) matches the reference plane of implant orientation measurements provided to the surgeon. The orientation of the C-arm may coincide with a supine coronal plane or a horizontal plane defined in the coordinate system of the electronic guidance system, such electronic guidance system comprising the inclination sensor; alternatively, some surgeons prefer to align the C-arm with respect to the patient based on other considerations, cues, techniques, etc. For example, some surgeons may align the C-arm plane with some amount of tilt by default. The tilt angle of the C-arm may be obtained from the C-arm equipment.

The coronal plane is one of the three principle anatomical planes of the body. When the body is oriented in a supine position, the coronal plane is referred to as the supine coronal plane. In the direct anterior approach to THA, extreme care is taken to position the patient such that the supine coronal plane is parallel to the ground, as surgeons often use this plane as an aid in positioning implants. In this orientation, the supine coronal plane is orthogonal to gravity.

The care taken in positioning the patient allows for the electronic guidance system to electronically register the supine coronal plane. If the sensor apparatus (comprising the optical sensor and the inclination sensor) is attached to a patient's pelvis when this plane is registered at the commencement of the surgical procedure, the defined coordinate system in which all measurements are provided is fixed to the patient's pelvis.

As described, the electronic guidance system may further be capable of measuring inclination with the use of the inclination sensor (e.g. accelerometer). Because the sensor apparatus (comprising the optical sensor and inclination sensor) is mounted to the patient's pelvis, changes in inclination of the inclination sensor correspond to changes in inclination of the pelvis. When the patient's supine coronal plane is substantially orthogonal to gravity, inclination measurements from the inclination sensor may be used to register the supine coronal plane. The optical sensor and inclination sensor may be co-registered to provide both optical measurements and inclination measurements in a common co-ordinate system. The inclination measurements provide up to two degrees of freedom in orientation, which may be used to register a horizontal plane of the defined coordinate system of the electronic guidance system. Careful patient positioning allows for the supine coronal plane to be equated to this horizontal plane.

During registration of the APP, the computing unit of the electronic guidance system may further use inclination measurements to register the supine coronal plane of the patient. Registration of these two planes—the APP and the horizontal plane—further enables the instructions executing on the computing unit to calculate the patient's supine pelvic tilt, a value that the surgeon can view on a GUI, by computing the angle of the APP relative to the supine coronal plane.

Additional planes of reference for acetabular cup implant measurements include the patient's standing coronal plane i.e. the plane that divides the patient's body into a front and back portion illustrated in FIG. 10b. Compared to the standing position, the supine position results in a weaker gravitational load on the spine causing pelvic tilt to vary when standing and when supine. Pelvic tilt measured from a lateral X-ray image of a pelvis is typically with respect to a patient's standing coronal plane. In some cases, the surgeon may wish to place the acetabular implant using the patient's standing pelvic tilt. In the direct anterior approach to THA, it is not possible to directly register the patient's standing APP as the patient is positioned supine on the OR table.

Figure 11:
FIG. 11 shows a graphical user interface (GUI) displayed on a display screen of a computing unit assisting a surgeon to provide input of a standing pelvic tilt angle.

Prior to beginning the procedure, the patient's pelvic tilt can be measured on the X-ray images and the standing pelvic tilt can be determined. The surgeon may enter the pelvic tilt manually on the computing unit, which may execute instructions to provide a feature that enables the surgeon to input, on a GUI, the patient's standing pelvic tilt obtained from pre-operative x-rays. This feature may be a step in a basic surgical workflow, or an optional step shown on a different screen. An example of this GUI is shown in FIG. 11. Such a command may include, but is not limited to, pressing a specified button on a human machine interface (HMI). The GUI may provide instructions on how to use the HMI to input the standing pelvic tilt angle.

Alternatively, a PACS (picture archiving and communication system) may electronically provide the X-ray image and a value for standing pelvic tilt to the computing unit of the electronic guidance system. Alternatively, an image analyzer communicatively coupled to the computing unit may calculate standing pelvic tilt from the standing lateral X-ray or allow a surgeon to manually identify landmarks on the X-ray, such landmarks then used for a calculation of pelvic tilt to make it fast and easy for the surgeon to obtain the patient's standing pelvic tilt for a direct anterior THA procedure.

In an exemplary embodiment of an electronic guidance system used during an implant placement procedure, once the standing pelvic tilt has been provided to the computing unit through the HMI (or calculated as described from a pre-operative image), a reference plane is generated using the inputted tilt angle and the APP. The APP must be registered, for example, using previously described techniques. The system will progress through the procedure, referencing all acetabular cup orientation measurements to the standing coronal plane, by compensating the APP as registered with the user's inputted standing pelvic tilt.

Mathematically, the acetabular cup orientation measurements are expressed as two Euler angles (known as inclination and anteversion) within a particular coordinate frame. The "compensation" of the APP may occur as follows: the APP is generated or calculated in a coordinate frame, and a rotation is applied to this coordinate frame by the amount of inputted standing pelvic tilt. The two Euler angles are then expressed and displayed to a surgeon within the resulting post-rotation coordinate frame.

The electronic guidance system calculates multiple transformations in up to 6 degrees of freedom between each of the anatomy, the surgical instrument, the sensor apparatus and the target in order to provide the surgeon with acetabular cup orientation measurements. These measurements are between the anatomy of the patient and the impactor tool that is used to place the acetabular cup.

By calculating registration matrices between the sensor apparatus and the anatomy, the target and the tool, and by using pose information from the target, instructions executing on the computing unit can calculate the orientation measurements between the tool and the patient. The calculations are explained below:

$R_{PI}$—The orientation of the cup implant relative to the pelvis. Inclination and anteversion angles are calculated from this matrix.
$R_{CP}$—The registration matrix from the sensor to the pelvis.
$R_{CB}$—The orientation portion of the current pose of the target, updated in real-time.
$R_{BI}$—The relationship between the target and the tool.

$$R_I^P = (R_P^C)^T \, R_B^C \, R_I^B$$

$$R_I^P = \begin{bmatrix} r_{(1,1)} & r_{(2,1)} & r_{(3,1)} \\ r_{(2,1)} & r_{(2,2)} & r_{(3,2)} \\ r_{(3,1)} & r_{(2,3)} & r_{(3,3)} \end{bmatrix}$$

$$\text{operative inclination} = \theta = \text{pitch}(R_I^P)$$
$$= \text{atan2}\left(-r_{(3,1)}, \sqrt{r_{(3,2)}^2 + r_{(3,3)}^2}\right)$$
$$\text{operative anteversion} = \psi = \text{yaw}(R_I^P)$$
$$= \text{atan2}(r_{(2,1)}, r_{(1,1)})$$
$$\text{radiographic inclination} = \text{atan}\left(\frac{\tan(\theta)}{\cos(\psi)}\right)$$
$$\text{radiographic anteversion} = \text{asin}(\cos(\theta)\sin(\psi))$$

Once pelvic tilt is provided, one of these registration matrices, $R_{CP}$, is modified by a matrix that corresponds to pelvic tilt. The following equations disclose the calculations performed by the computing unit to apply a pelvic tilt to a registration coordinate frame.

$$R_{CP\text{-}modified} = R_{CP} R_{tilt}$$

In other cases, the surgeon may not wish to place the acetabular implant with reference to the patient's standing pelvic orientation, but rather use the registered APP as a reference plane for placement of the acetabular cup implant.

In such cases, the surgeon is able to proceed through the workflow without encountering the GUI requesting the input of the patient's standing pelvic tilt as long as the implant orientation measurements are set to be, by default, displayed with respect to the APP. The system will progress through the procedure, referencing all acetabular cup orientation measurements to the APP that is registered at the beginning of the procedure. Optionally, as described above, inclination measurements of the inclination sensor may further be used to register a supine coronal plane of the patient and all acetabular cup orientation measurements may be referenced to the supine coronal plane.

Similarly, a surgeon may use the tilt angle of the C-arm to obtain measurements with respect to the C-arm plane as a reference plane.

Figure 12:
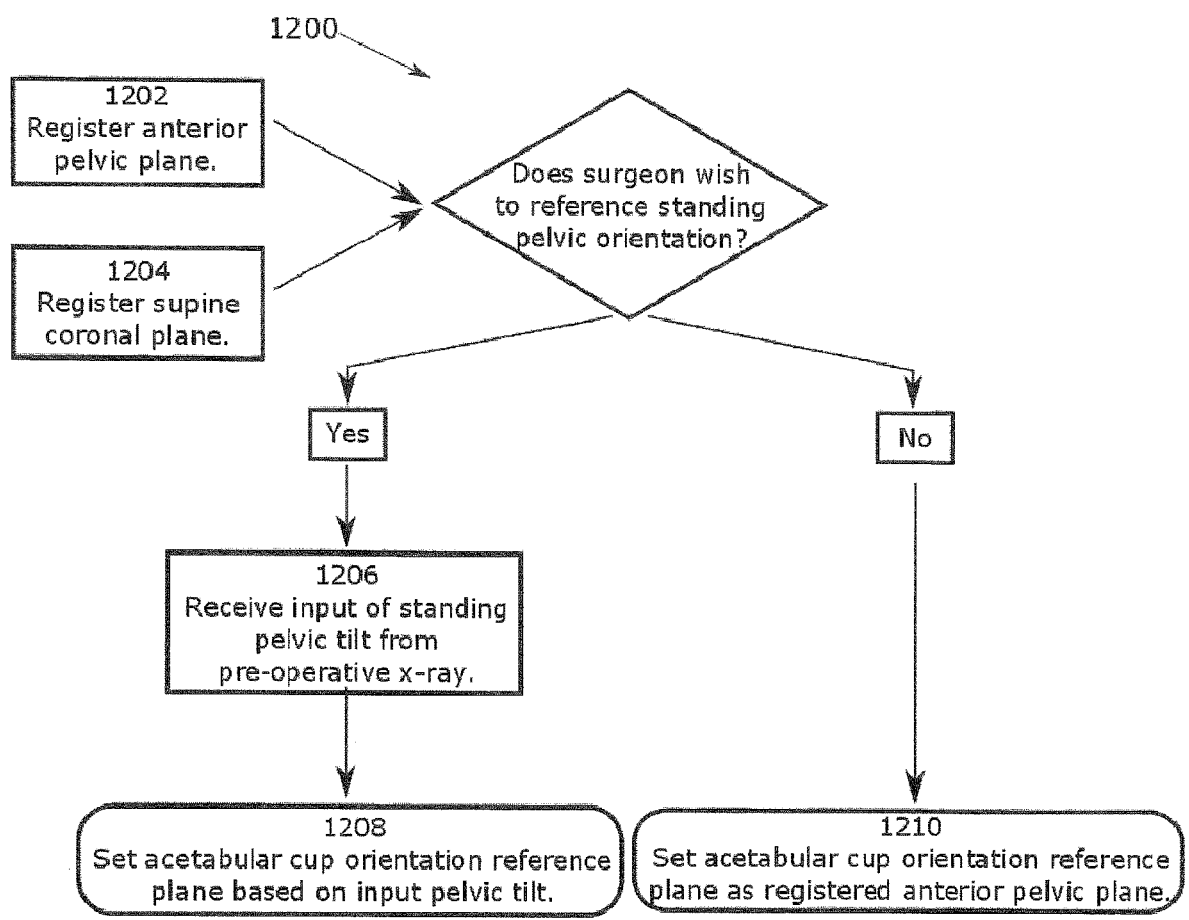
FIG. 12 depicts a method of anatomical registration that compensate for pelvic tilt with respect to registered anatomical planes.

An exemplary workflow to perform anatomical registration in Direct Anterior Approach to THA and a method for providing the surgeon with an optional means to reference the patient's standing pelvic orientation during THA has been presented herein. FIG. 12 illustrates the disclosed computer-implemented method 1200 of calculating and displaying acetabular cup orientation measurements with respect to the APP and supine coronal plane. At step 1202, the anterior pelvic plane is registered. At step 1204, the supine coronal plane is registered. The APP, the supine coronal plane and the associated implant orientation measurements may be displayed the user. If the surgeon desires to provide pelvic tilt input to the computing unit, the instructions executing on the computing unit may execute instructions to receive the input (for a pre-operative X-ray, if applicable) at step 1206 and calculate and display implant orientation measurements of the acetabular cup implant with respect to the standing coronal plane 1208. If such input is not available, implant orientation measurements, by default, may be provided with respect to the anterior pelvic plane 1210. The computing unit is executing instructions that allow the surgeon to change the reference plane and view implant orientation measurements instantaneously. If the surgeon decides to change the inputted tilt angle, the surgeon may do so without re-registering the patient's anatomical planes.

A method of anatomical registration that provides surgeons with the option to reference to the patient's standing pelvic orientation during THA procedures has been described herein in the context of the direct anterior approach to THA. This method is capable of being applied to all surgical approaches to THA as similar pre-operative x-rays are performed and made available in all approaches, providing the surgeon with the patient's standing pelvic orientation throughout the duration of the procedure.

Figure 13A:
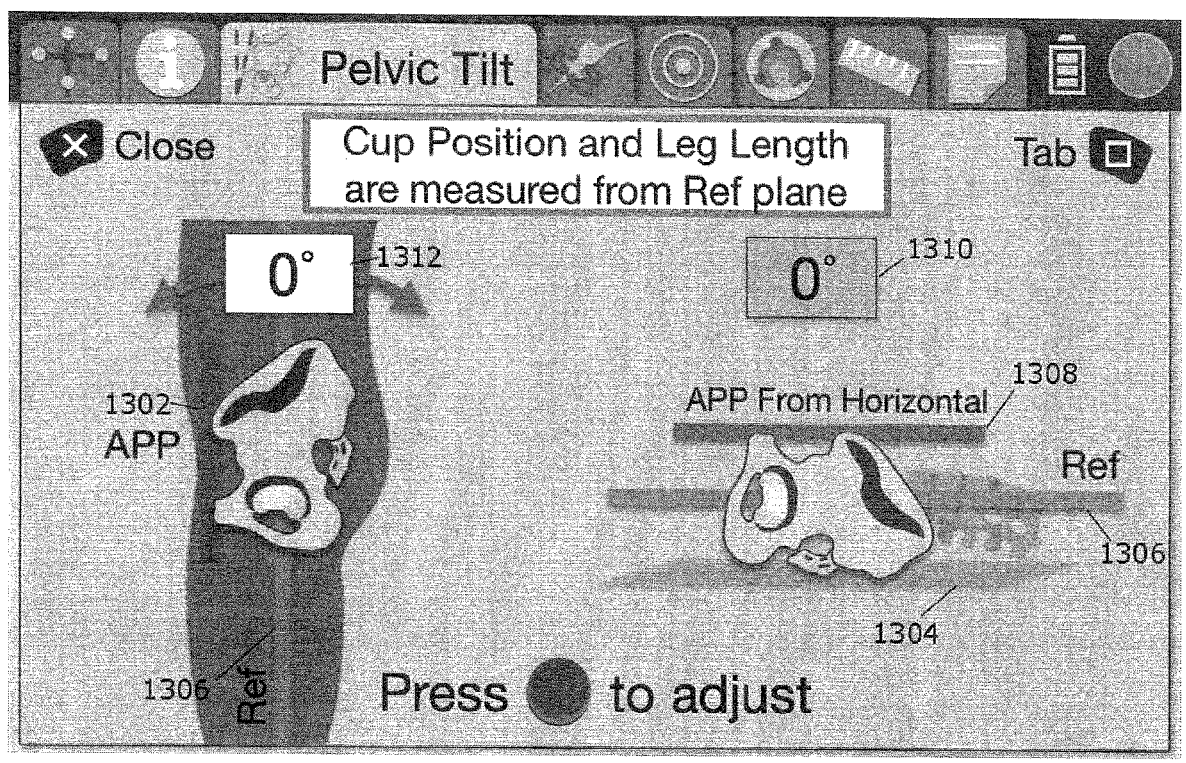
FIG. 13a-13f show a GUI displaying various reference planes available to a surgeon to reference acetabular cup orientation measurements.

Reference is now made to FIG. 13a-13f. FIG. 13a shows a GUI on a computing unit, as an example for clarity, displaying reference planes available to the surgeon for calculating implant orientation measurements. A surgeon has registered the patient's APP 1302 using optical measurements and the horizontal plane 1304 using inclination measurements. The horizontal plane 1304 corresponds to a plane orthogonal to gravity as calculated from inclination measurements. A Ref plane 1306 corresponds to a plane in the defined coordinate system of the electronic guidance system. The Ref plane 1306 is provided as a graphical aid for surgeons to visualize the reference plane used for acetabular cup orientation measurements. In FIGS. 13a-13f, there are two planes marked as Ref plane 1306. This is done to express information as simply as possible to the surgeon and in multiple representations to facilitate use of the system by surgeons who may prefer one representation over the other.

Some surgeons prefer to visualize anatomical planes while the patient is standing while others prefer to visualize planes with the patient lying supine. A measurement of the angle between APP 1302 and horizontal plane 1304 is depicted by the angle of the line 1308 with respect to horizontal plane 1304. In this Figure, an APP 1302 and a horizontal plane 1304 are parallel. This angle is also calculated and displayed as a tilt angle in Box 1310. Box 1312 is a tilt angle that can be modified by a user.

Figure 13B:
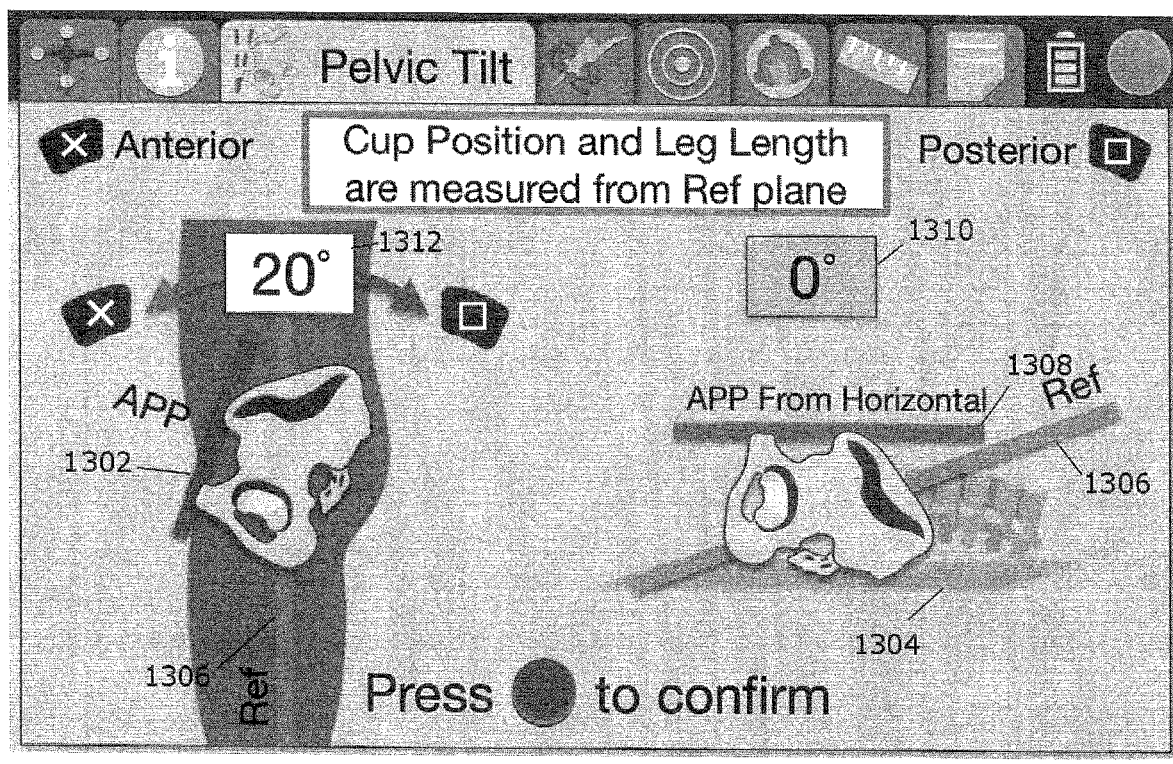

In FIG. 13*b*, the surgeon provides a posterior tilt angle of 20 degrees in Box 1312 and enters the value from a HMI. The Ref plane 1306 is generated and displayed at an angle of 20 degrees from the APP 1302. The surgeon may view the resulting acetabular cup orientation measurements with this tilt angle.

Figure 13C:
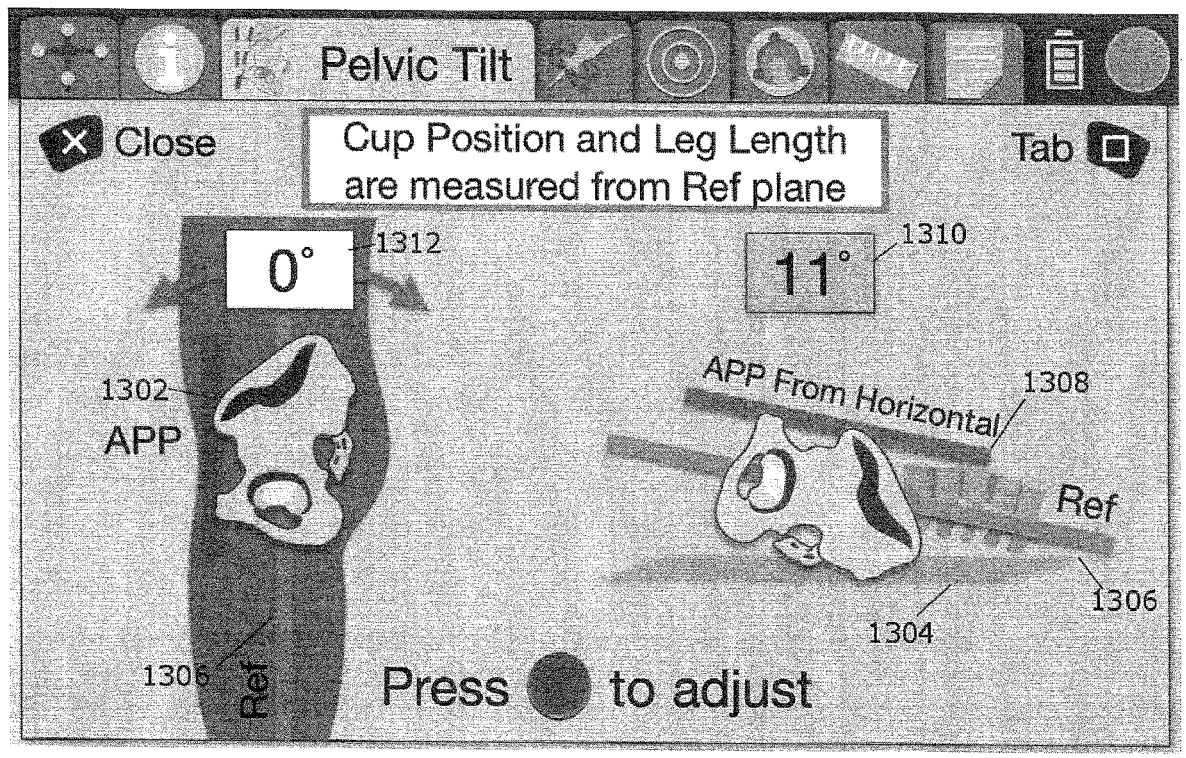

In FIG. 13*c*, the angle between the APP and the horizontal plane is calculated to be the supine pelvic tilt and displayed in Box 1310 to be 11 degrees. The default inputted tilt angle in Box 1312 is 0 degrees. Acetabular cup orientation measurements are, by default, provided with respect to the APP. The surgeon may view the resulting acetabular cup orientation measurements with this tilt angle.

Figure 13D:
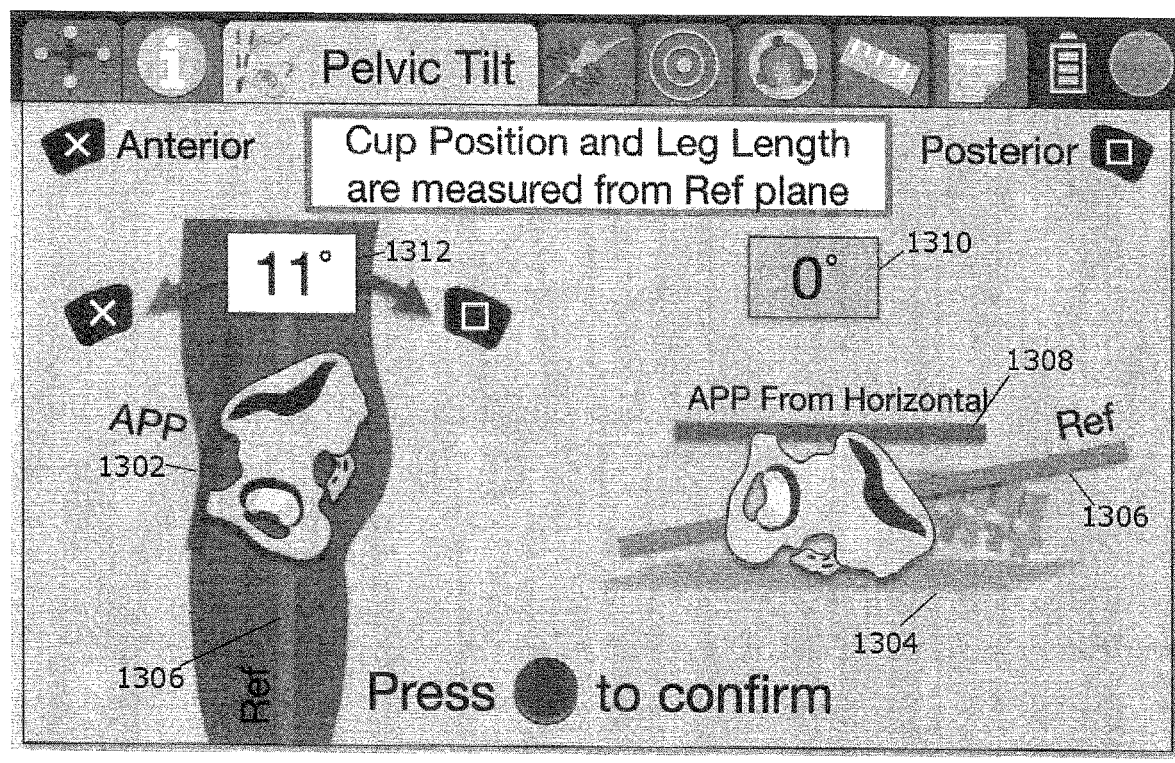

In FIG. 13*d*, the surgeon enters an inputted tilt angle in Box 1312 of 11 degrees and the computing unit executes instructions to generate the Ref plane 1306 at an angle of 11 degrees from APP 1302. The supine pelvic tilt is calculated in Box 1310 to be 0 degrees since APP 1302 is parallel to horizontal 1304. The surgeon may view the resulting acetabular cup orientation measurements with this tilt angle.

Figure 13E:
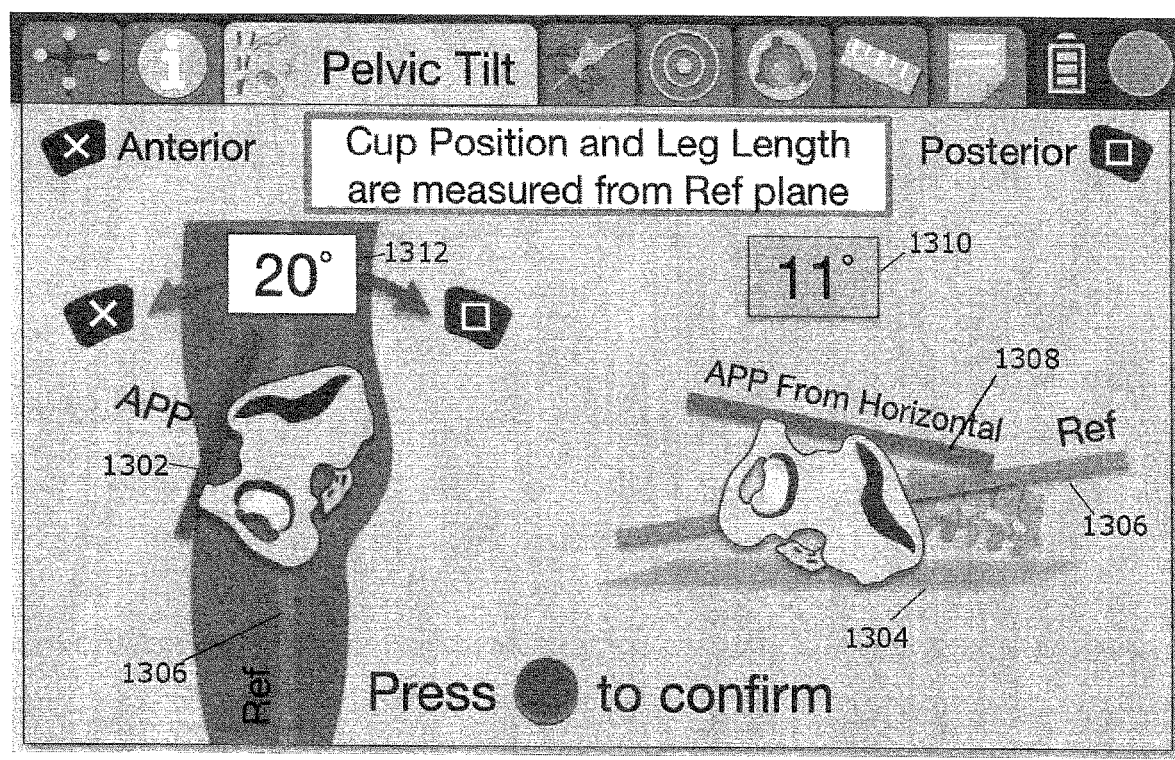

In FIG. 13*e*, the surgeon enters an inputted tilt angle in Box 1312 of 20 degrees and the computing unit executes instructions to generate the Ref plane 1306 at an angle of 20 degrees from the APP 1302. The angle of 20 degrees may be an arbitrary choice by the surgeon, or obtained from pre-operative medical images or set in accordance to how a surgeon would line up a C-arm (or other intra-operative x-ray) with respect to the patient's position on the operating table. The surgeon may view the resulting acetabular cup orientation measurements with this tilt angle.

Figure 13F:
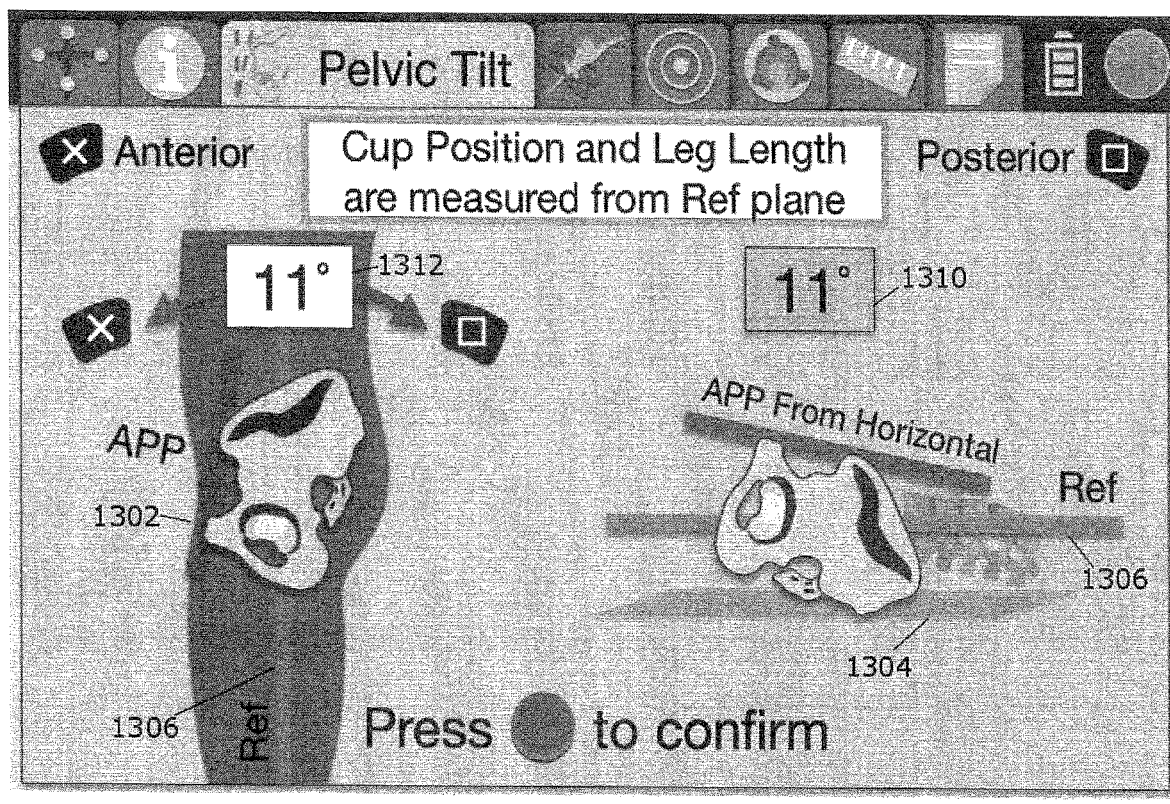

In FIG. 13*f*, the surgeon enters an inputted tilt angle in Box 1312 of 11 degrees to match the supine pelvic tilt. The supine pelvic tilt is calculated, and displayed in Box 1310, to be 11 degrees. Thus, the computing unit generates and displays Ref plane 1306 parallel to horizontal 1304 and displays acetabular cup orientation measurements with respect to the Ref plane 1306. The surgeon may view the resulting acetabular cup orientation measurements with this tilt angle.

Figure 13G:
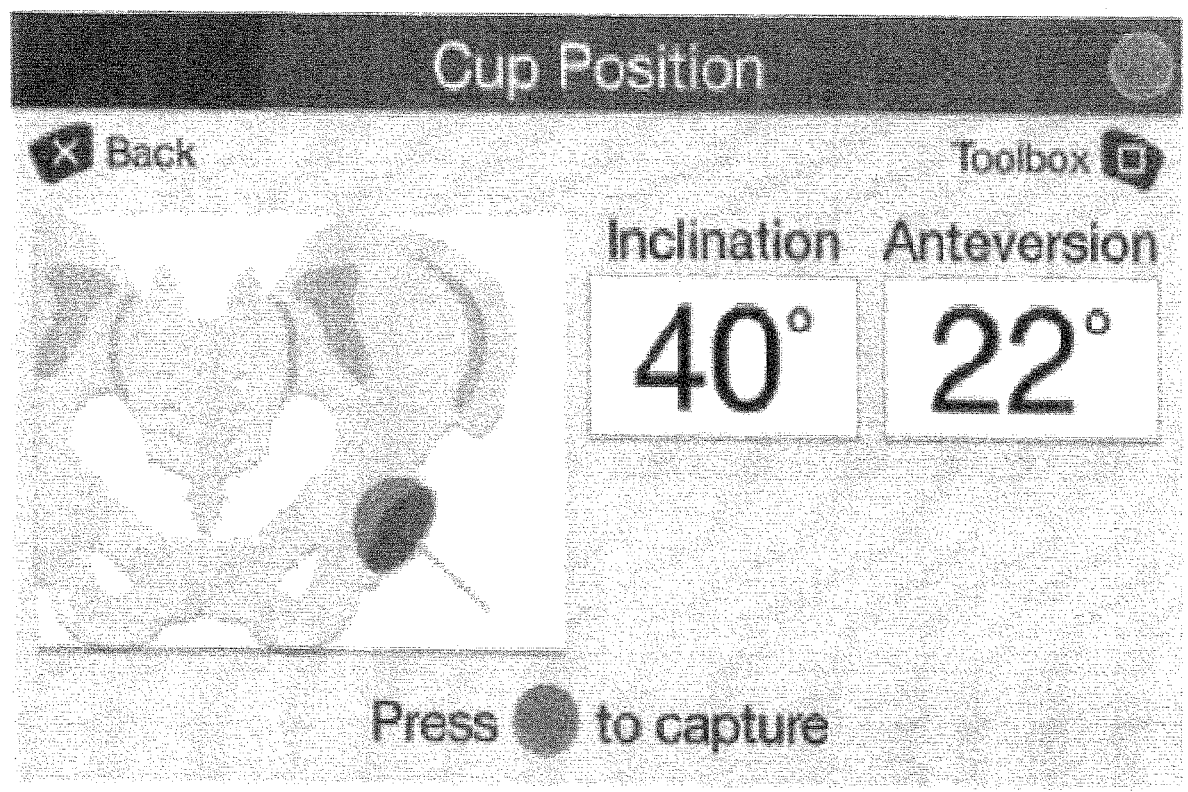
FIG. 13g shows a GUI displaying acetabular cup orientation measurements to a surgeon, as an example for clarity.

Once the reference plane has been modified by the surgeon to adjust for the inputted tilt angle as described in FIGS. 10*a*-10*e*, implant orientation measurements are immediately provided to the surgeon with respect to the Ref plane. FIG. 13*g* shows a GUI, as an example for clarity, on a computing unit displaying the values of implant orientation measurements after being compensated for the inputted tilt angle, if provided. The surgeon may modify the inputted tilt angle at any time to re-calculate the implant orientation measurements. This feature is advantageous as the surgeon may conduct several trails before deciding on a final implant.

Therefore, this variation enables a surgeon to orient an acetabular implant (by tracking an impactor or inserter in real-time with respect to a reference plane of choice), to measure the supine pelvic tilt and to view in real-time implant orientation measurements of the acetabular cup implant to account for a patient's standing pelvic tilt or any other angle.

III. Calculating Leg Length and Offset Measurements

There are several techniques known in the art to calculate leg length and offset parameters for THA, some of which are discussed in U.S. Pat. No. 9,247,998. In the present specification, it is disclosed that for a THA performed using the direct anterior approach, as the patient is lying supine, the electronic guidance system provides guidance to the surgeon to probe locations on the patient's operative leg in order to determine the change in leg length and offset.

Figure 14:
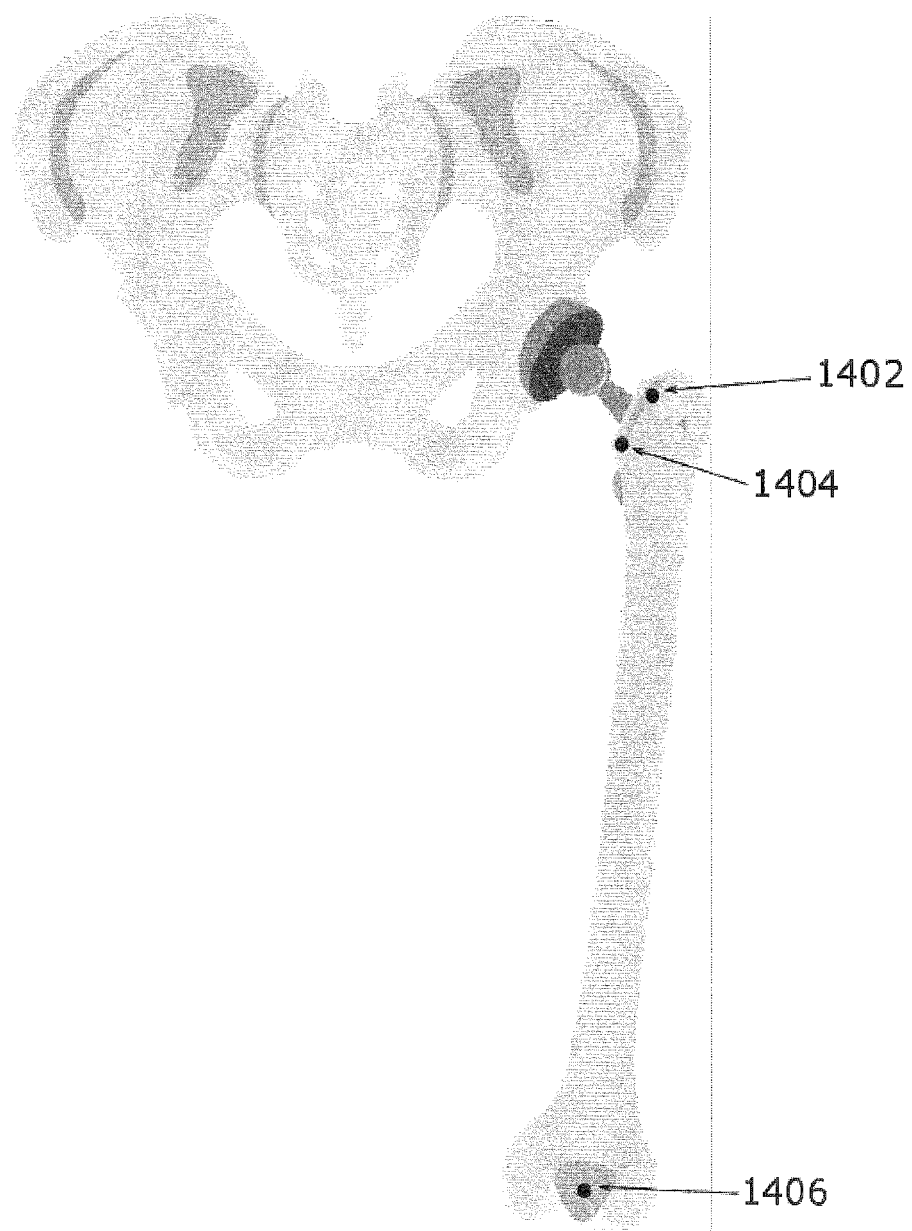
FIG. 14 depicts an anatomy of a patient's leg comprising a pelvis and a femur showing points on the leg that may be probed during calculation of leg length in a THA.

Reference is now made to FIG. 14. Three points on a patient's leg—lateral 1402, medial 1404 and distal 1406—are probed in a pre-operative, baseline position before dislocating the hip joint. The same three points on the leg are probed in a final position after the prosthetic implant has been placed in the patient's pelvis and femur. Due to the presence of soft tissue on at least two of the three points within the surgical incision and the presence of skin on the distal point of the leg, it may be challenging for a surgeon to locate the same three points for baseline and final position with high precision. To reduce errors in the capture of points in both positions of the leg—baseline and final—that are used to calculate the change in leg length and offset measurements, disclosed herein are some hardware or software solutions to assist a user in probing the same three points.

In order to prevent the user from obtaining incorrect results due to errors in re-locating the same points on the leg, the instructions executing on the computing unit may perform additional checks and provide guidance to a surgeon as or immediately after each point is probed in the baseline and final position. Such immediate guidance allows the system to provide feedback to the surgeon as the points are being captured and allows the surgeon to re-capture any points, if necessary. Such checks include, but are not limited to, calculating the distance between each point to ensure that the result meets a set criterion; capturing a first of a series of points during a particular step of the procedure to ensure that any inadvertent movements of the leg during the step will not result in invalid measurements; providing guidance to the user to space out the probed points on the leg to allow for more accurate measurements, etc.

Figure 15A:
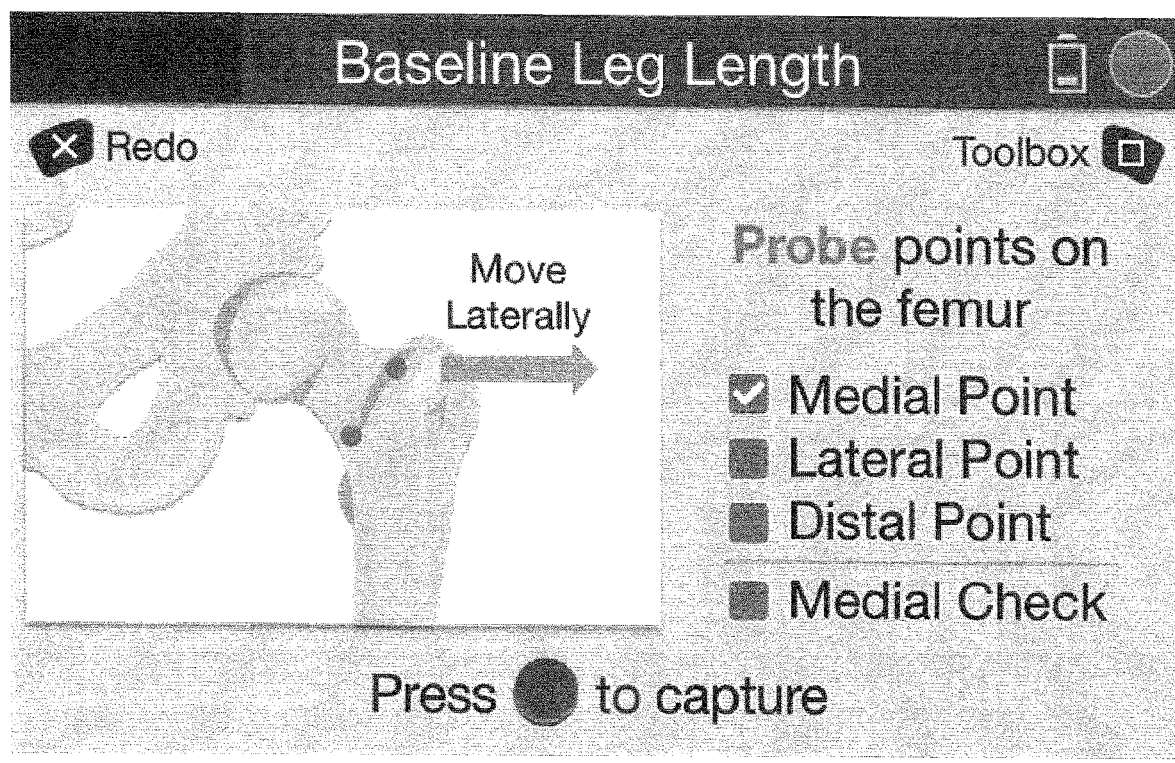
FIGS. 15a and 15b show a GUI displaying directional guidance provided to a surgeon during probing of points on a leg, as an example for clarity.
Figure 15B:
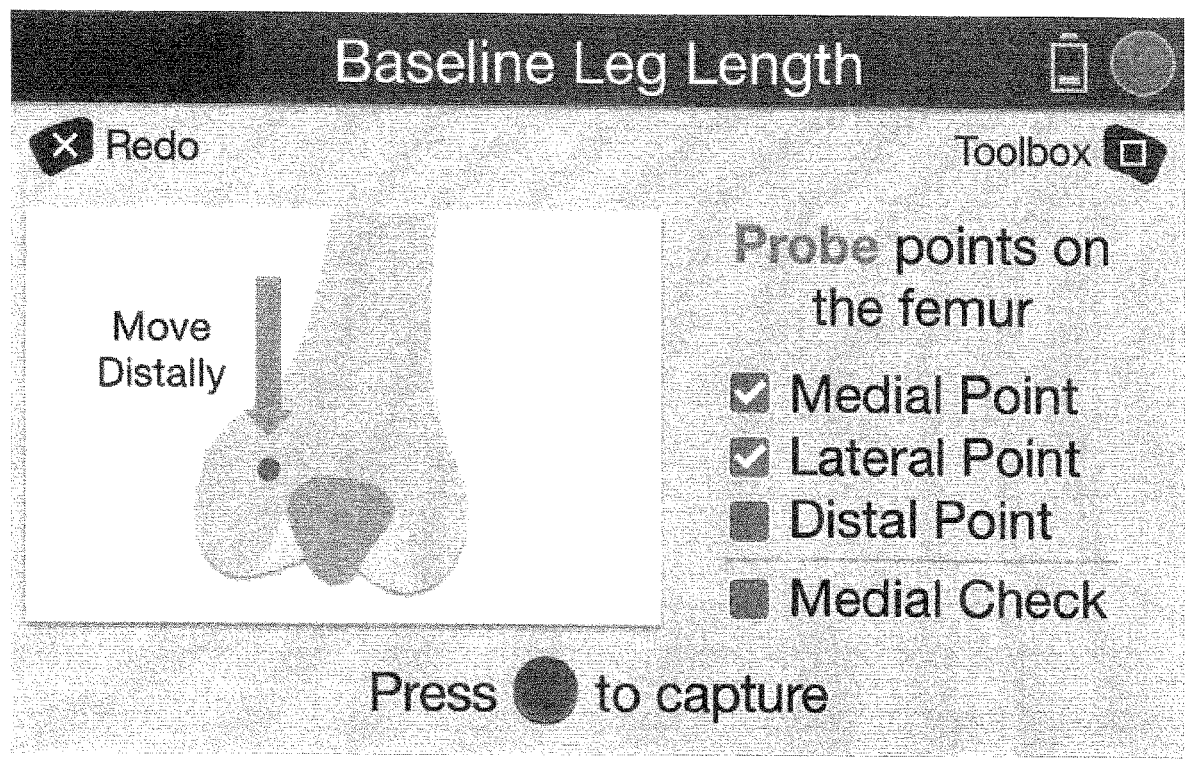

Reference is now made to FIGS. 15*a* and 15*b* depicting a GUI that provides directional guidance to the user, as the user is probing points on the patient's leg during baseline and final leg position to calculate change in leg length and offset measurements.

Other checks implemented by instructions executing on the computing unit include; calculating the distances between each pair of the three points of the baseline and final position to ensure that the correct points were probed during final measurement; calculating an angle formed by the lateral, medial and distal points and verifying that the angle in baseline position is similar to the angle in final position, etc. If any of the checks are above a set threshold, the calculation of leg length may be deemed invalid.

Some operations to calculate a fit metric and an angle metric are disclosed below:

$$\text{Fit metric} = \frac{\sum_{i=1}^{3} |p_{ci} - p_{bi}|}{3}$$

Where $p_{ci}$ and $p_{bi}$ are points captured in final and baseline leg positions, respectively.

$$v^*_1 = p^*_3 - p^*_2$$

$$v^*_2 = p^*_1 - p^*_2$$

$$\theta_* = a\cos(v^*_1 \cdot v^*_2)$$

$$\text{Angle metric} = |\theta_1 - \theta_2|$$

Where $v_1$ is the angle created by a vector between the medial point 1404 and lateral point 1402, $v_2$ is the angle created by a vector between the medial point 1404 and distal point 1406, and $\theta_1$ and $\theta_2$ are the angles calculated in baseline leg position and final leg position respectively.

Using measurements of pre- and post-operative center of rotation of the hip joint, instructions executing on the computing unit may allow for calculation of implant orientation measurements without instructing a user to return the patient's leg to the baseline position.

Figure 16A:
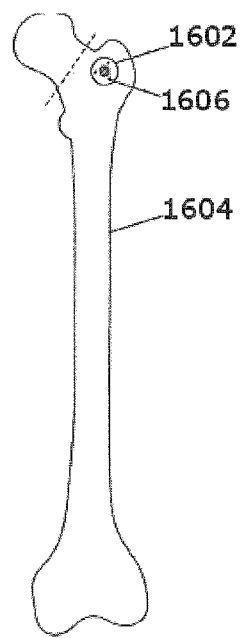
FIGS. 16a, 16b and 16c show femoral platforms on a femur used to capture points on a leg.
Figure 16B:
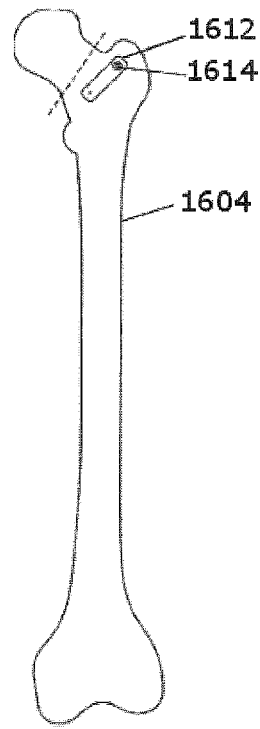
Figure 16C:
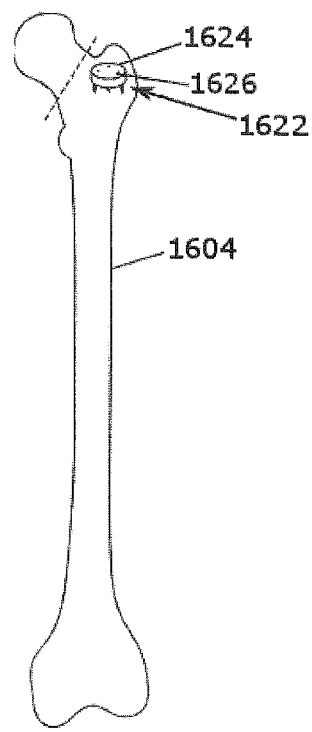

Additionally, hardware solutions may be provided to reduce any errors introduced by probing an incorrect location on the leg. Reference is now made to FIGS. 16*a*, 16*b* and 16*c*. FIG. 16*a* depicts a single screw 1602 that may be placed on the anterior greater trochanter of the operative leg or any other location on the leg that provides landmarks or divots on a visible and repeatable surface for probing. The landmarks are separated by a difference in positional relationship that is known to the computing unit (e.g. pre-stored in a database). This is an expected positional relationship between the landmarks provided the leg remains stationary. The screw may be small in size and easily installed on a range of patients, through the miniature incision of the direct anterior approach as long as the screw does not interfere with the femoral implant. In operation, when a surgeon probes each landmark on the screw, the computing unit executes instructions that calculate an actual difference in positional relationship of the landmarks. If the actual difference in positional relationship and expected difference in positional relationship do not match, the computing unit may alert the user of potential errors, for example, due to movement of the leg between probing of the respective landmarks.

FIG. 16*b* shows a femoral platform 1612 that comprises at least two divot locations 1614 that correspond to a medial point and a lateral point shown in FIGS. 15*a* and 15*b* and have a known positional relationship between each divot location. In operation, the femoral platform is used similar to the screw illustrated in FIG. 16*a*. The femoral platform also has the advantage of being small in size and is easily installed on a range of patients as the distance between the medial and lateral points is typically only approximately 10-15 millimeters.

FIG. 16*c* depicts another hardware solution to reduce errors due to the probing of incorrect points. There is shown a femur platform 1622 with a top end comprising a circular disc 1624 and a bottom end comprising a bone attachment mechanism (for example, spikes with a sharp distal end that can pierce through bone). The disc comprises multiple landmarks or features 1626 for probing. The positional relationship between each of the landmarks or features for probing may be known to the instructions executing on the computing unit.

Various embodiments have been described herein with reference to the accompanying drawings. It will, however, be evident that various modifications and changes may be made thereto, and additional embodiments may be implemented, without departing from the broader scope of the disclosed embodiments as set forth in the claims that follow.

We claim:

1. An electronic guidance system to provide intra-operative anatomic measurements to guide placement of an implant with respect to an anatomy of a patient, the electronic guidance system comprising:

an optical sensor to generate and communicate image data of respective targets attached to a probe tool and a surgical tool to track the probe tool and the surgical tool during an implant placement procedure;

an intra-operative computing unit communicatively coupled to the optical sensor, the intra-operative computing unit configured to:

register a first reference plane for the anatomy of the patient in a defined coordinate system using the respective image data from the probe tool, where the probe tool points to at least three reference locations on the anatomy to define the first reference plane;

provide a user interface to display the first reference plane;

receive an inputted tilt angle of the anatomy of the patient relative to a second plane within the defined coordinate system;

generate a second reference plane for the anatomy of the patient using the inputted tilt angle and the first reference plane;

update the user interface to display the second reference plane, responsive to the inputted tilt angle;

determine implant orientation measurements using the respective image data from the surgical tool as it is tracked during the implant placement procedure, referencing the implant orientation measurements relative to the second reference plane; and display in the user interface the implant orientation measurements relative to the second reference plane.

2. The system of claim 1 wherein the intra-operative computing unit is further configured to:

determine implant orientation measurements relative to the first reference plane using the respective image data from the surgical tool as it is tracked, referencing the implant orientation measurements to the first reference plane for the anatomy of the patient without using the inputted tilt angle; and display in the user interface the implant orientation measurements relative to the first reference plane.

3. The system of claim 1 further comprising:

an inclination sensor to generate and communicate inclination measurements to track the anatomy of the patient during the implant placement procedure where changes in inclination of the inclination sensor correspond to changes in inclination of the anatomy of the patient and the intra-operative computing unit is further configured to register a positional plane for the anatomy of the patient in the defined coordinate system using the inclination measurements, equating the positional plane to a horizontal plane within the defined coordinate system.

4. The system of claim 3 wherein the intra-operative computing unit is further configured to:

calculate and display a tilt angle of the anatomy of the patient relative to the horizontal plane using the first reference plane and the positional plane.

5. The system of claim 3, wherein the inclination sensor comprises an accelerometer.

6. The system of claim 1 wherein the second plane is a standing coronal plane.

7. The system of claim 1 wherein the anatomy of the patient is a pelvis.

8. The system of claim 7 wherein the inputted tilt angle is a pelvic tilt determined from a pre-operative medical image of the pelvis.

9. The system of claim 1 wherein the first reference plane is the anterior pelvic plane determined when the patient is in a supine position.

10. The system of claim 1 wherein the intra-operative computing unit is further configured to provide the user interface to receive and display the inputted tilt angle.

11. The system of claim 1 wherein the intra-operative computing unit is further configured to receive the inputted tilt angle from an image analyzer communicatively connected to the intra-operative computing unit.

12. An electronic guidance system to provide intra-operative anatomic measurements to guide placement of an implant with respect to an anatomy of a patient, the electronic guidance system comprising:
   an optical sensor to generate and communicate image data of respective targets attached to a probe tool and a surgical tool to track the probe tool and the surgical tool during an implant placement procedure;
   an inclination sensor to generate and communicate inclination measurements where changes in inclination of the inclination sensor correspond to changes in inclination of the anatomy of the patient to track the anatomy of the patient during the implant placement procedure;
   an intra-operative computing unit communicatively coupled to the optical sensor and the inclination sensor, the intra-operative computing unit configured to:
      register a positional plane for the anatomy of the patient in a defined coordinate system using the inclination measurements, equating the positional plane to a horizontal plane within the defined coordinate system;
      provide a user interface to display the positional plane;
      receive an inputted tilt angle of the anatomy of the patient relative to a second plane within the defined coordinate system;
      generate a second reference plane for the anatomy of the patient using the inputted tilt angle and the positional plane;
      update the user interface to display the second reference plane, responsive to the inputted tilt angle;
      determine implant orientation measurements using the respective image data from the surgical tool as it is tracked during the implant placement procedure, referencing the implant orientation measurements relative to the second reference plane; and
      display, in the user interface, the implant orientation measurements relative to the second reference plane.

13. A computer implemented method to provide intra-operative anatomic measurements to guide placement of an implant, the method comprising the steps of:
   registering, by at least one processor of an intra-operative computing unit, a first reference plane for an anatomy of a patient in a defined coordinate system using image data of a probe tool, where the probe tool points to at least three reference locations on the anatomy to define the first reference plane, the image data received from an optical sensor configured to generate and communicate image data of respective targets attached to the probe tool and a surgical tool to track the probe tool and surgical tool during an implant placement procedure;
   providing a user interface to display the first reference plane;
   receiving, by the at least one processor, an inputted tilt angle of the anatomy of the patient relative to a second plane within the defined coordinate system;
   generating, by the at least one processor, a second reference plane for the anatomy of the patient using the inputted tilt angle and the first reference plane;
   updating the user interface to display the second reference plane, responsive to the inputted tilt angle;
   determining, by the at least one processor, implant orientation measurements using the respective image data from the surgical tool as it is tracked during the implant placement procedure, referencing the implant orientation measurements relative to the second reference plane; and
   displaying, by the at least one processor, in the user interface, the implant orientation measurements relative to the second reference plane.

14. The method of claim 13 further
   receiving, by the at least one processor, inclination measurements from an inclination sensor configured to generate and communicate inclination measurements to track the anatomy of the patient during the implant placement procedure where changes in inclination of the inclination sensor correspond to changes in inclination of the anatomy of the patient and
   registering, by the at least one processor, a positional plane for the anatomy of the patient in the defined coordinate system using the inclination measurements, equating the positional plane to a horizontal plane within the defined coordinate system.

15. The method of claim 14 further calculating and displaying, by the at least one processor, a tilt angle of the anatomy of the patient relative to the horizontal plane using the first reference plane and the positional plane.

16. The method of claim 13 wherein the second plane is a standing coronal plane.

17. The method of claim 13 wherein the anatomy of the patient is a pelvis.

18. The method of claim 17 wherein the inputted tilt angle is a pelvic tilt determined from a pre-operative medical image of the pelvis.

19. The method of claim 13 wherein the first reference plane is the anterior pelvic plane determined when the patient is in a supine position.

20. The method of claim 13 further providing, by the at least one processor, the user interface to receive and display the inputted tilt angle.

21. The method of claim 13 further receiving, by the at least one processor, the inputted tilt angle from an image analyzer communicatively connected to the at least one processor.

* * * * *